United States Patent [19]
Lehmann et al.

[11] Patent Number: 5,939,281
[45] Date of Patent: Aug. 17, 1999

[54] DETECTING ALLOREACTIVITY

[75] Inventors: Paul V. Lehmann; Alexey Karulin, both of Cleveland Heights; Richard Peter Trezza, Orange Village, all of Ohio

[73] Assignee: Case Western Reserve University, Cleveland, Ohio

[21] Appl. No.: 08/714,728

[22] Filed: Sep. 16, 1996

[51] Int. Cl.$^6$ .................................................. G01N 33/53
[52] U.S. Cl. ...................... 435/7.94; 436/501; 436/518; 436/531
[58] Field of Search ................................... 435/7.1, 7.24, 435/7.92, 29, 7.94; 436/501, 518, 531

[56] References Cited

U.S. PATENT DOCUMENTS

| | | |
|---|---|---|
| 4,879,374 | 11/1989 | Cerretti et al. . |
| 4,894,333 | 1/1990 | Cerretti et al. . |
| 4,948,442 | 8/1990 | Manns . |
| 4,968,607 | 11/1990 | Dower . |
| 5,047,215 | 9/1991 | Manns . |
| 5,200,312 | 4/1993 | Oprandy . |

FOREIGN PATENT DOCUMENTS

| | | |
|---|---|---|
| 0418014A1 | 3/1991 | European Pat. Off. . |

OTHER PUBLICATIONS

Taguchi et al., J. of Immunological methods, vol. 128, 65–73, Apr. 1990.

J.D. Sedgwick and P.G. Holt, "A Solid–Phase Immunoenzymatic Technique for the Enumeration of Specific Antibody–Secreting Cells," J. Immunol. Meth. 57:301–309 (1983).

B.D. Mazer et al., "An ELISA Spot Assay for Quantitation of Human Immunoglobin Secreting Cells," J. Allergy Clin. Immunol. 88:235–243 (1991).

H. Renz et al., "Enhancement of IgE Production by Anti–CD40 Antibody in Atopic Dermatitis," J. Allergy Clin. Immunol. 93:658–668 (1994).

T. Taguchi et al., "Detection of Individual Mouse Splenic T Cells Producing IFNγ and IL–5 Using the Enzyme–Linked Immunospot (ELISPOT) Assay," J. Immunol. Meth. 128:65–73 (1990).

F. Fujihashi et al., "Cytokine–Specific ELISPOT Assay," J. Immunol. Meth. 160:181–189 (1993).

Y. Miyahira et al., "Quantification of Antigen Specific CD8+ T Cells Using an ELISPOT Assay," J. Immunol. Meth. 181: 45–54 (1995).

B.C. Nayer and A.W. Adamson, "Contact Angle in Industry," Science Reporter pp. 76–79 (Feb. 1981).

T.J. Schall and K.B. Bacon, "Chemokines, leukocyte trafficking, and inflammation," Curr. Op. Immunol. 6:865–873 (1994).

G. Berke, "The CTL's Kiss of Death," Cell 81:9–12 (1995).

G. Gammon et al., "T Cell Determinant Structure: Cores and Determinant Envelopes in Three Mouse Major Histocompatibility Complex Haplotypes," J. Exp. Med. 173:609–617 (1991).

J.G. Tilles and M. Finland, "Microassay for Human and Chick Cell Interferons," Applied Micro. 16:1706–1707 (1968).

G.A. Molinaro et al., "Antigen–Secreting Cells: Enumeration of Immunoglobin–Allotype–Secreting Cells in Nonimmunized Rabbits by Means of Hybrid–Antibody–Coated Erythrocytes in a Reverse Hemolytic Plaque Assay," Proc. Nat. Acad. Sci. 71:1229–1233 (1974).

E. Gronowicz et al., "A plaque assay for all cells secreting Ig of a given type or class," Eur. J. Immunol. 6:588–590 (1976).

L.S. Lin et al., "Characterization of the Heterogenous Molecules of Human Interferons: Differences in the Cross–Species Antiviral Activities of Various Molecular Populations in Human Leukocyte Interferons," Virol. 39:125–130 (1978).

D. Primi et al., "A Hemolytic Plaque Assay for Activated Murine T Cells," J. Exp. Med. 150:987–1000 (1979).

P. Truffa–Bachi and G.R. Bordenave, "A Reverse Hemolytic Plaque Assay for the Detection and the Enumeration of Immunoglobin Allotype–Secreting Cells," Cell. Immunol. 50:261–270 (1980).

R. Palacios et al., "Production of human immune interferon (Hu IFN–γ) studied at the single cell level. Origin, evidence for spontaneous secretion and effect of cyclosporin A," Eur. J. Immunol. 13:221–225 (1983).

A. Zlotnik et al., "Characterization of the γ–Interferon–Mediated Induction of Antigen–Presenting Ability in P388D1 Cells," Journal Immunol. 131:2814–2820 (1983).

D.P. King and P.P. Jones, "Induction of Ia and H–2 Antigens on an Macrophage Cell Line by Immune Interferon," Journal Immunol. 131:315–318 (1983).

T.W. Chang et al., "Use of monoclonal antibodies as sensitive and specific probes for biologically active human γ–interferon," Proc. Nat. Acad. Sci. 81:5219–5222 (1984).

J. Kappler and P. Marrack, "Lymphokines," vol. 2: *Cellular Immunology*, Ch. 59 pp. 59.1–59.10 (1986).

C. Czerkinsky et al., "The Solid Phase Enzyme–Linked Immunospot Assay (ELISPOT) for Enumerating Antibody–Secreting Cells: Methodology and Applications," Chapter 10, pp. 217–240, *ELISA and Other Solid Phase Immunoassays: Theoretical and Practical Aspects* (1988).

(List continued on next page.)

*Primary Examiner*—Christina Chan
*Assistant Examiner*—Patrick Nolan
*Attorney, Agent, or Firm*—Medlen & Carroll, LLP

[57] ABSTRACT

The present invention relates to devices and methods for detecting cellular products, and in particular for measuring secreted cellular products, including cytokines. Microwells comprising hydrophobic membranes are described having greater capability to detect cytokines from individual cells in a mixture of heterogeneous cells. A method is provided that can serve as a) a functional predictor of allograft survival in transplant recipients, and b) a tool for monitoring the level of immunosuppression in allograft recipients.

15 Claims, 18 Drawing Sheets

OTHER PUBLICATIONS

J.D. Sedgwick and P.G. Holt, "ELISA–Plaque Assay for the Detection of Single Antibody–Secreting Cells," Chapter 11, pp. 241–2263, *ELISA and Other Solid Phase Immunoassays: Theoretical and Practical Aspects* (1988).

A.J.M. van den Eertwegh et al., In Vivo Kinetics and Characterization of IFN–γ–Producing Cells during a Thymus Independent Immune Response, J. Immunol. 147:439–446 (1991).

J. Aramburu et al., "Detection of double–stranded RNA by ELISA dot immunobinding assay using an antiserum to synthetic polynucleotides," J. Virol. Meth. 33:1–11 (1991).

J. Parrado et al., "Direct Quantitative Determination of Peptides and Proteins in PVDF Transfer Membrane Using a Computing Densitometer," Peptide Res. 6:13–16 (1993).

S. Tanguay and J.J. Killion, "Direct Comparison of ELISPOT and ELISA–Based Assays for Detection of Individual Cytokine–Secreting Cells," Lymphokine and Cytokine Res. 13:259–263 (1994).

J. Aniagolu et al., "Analysis of anticholesterol antibodies using hydrophobic membranes," J. Immunol. Meth. 182:85–92 (1995).

S. Ishizaka et al., "Detection of Soluble T Cell Receptor – Releasing Cells by ELISPOT Assay," J. Immunoassay 16:97–113 (1995).

Chouarb et al. (Dec. 1994) Proc. Natl. Acad. Sci. USA. vol. 91: 12659–12663.

Arvilommi H. (Jun. 1996) APMIS. vol. 104(6):401–10.

Merville et al. (Mar. 1993) Transplantation. vol. 55(3): 639–46.

Sedgwick et al. (1992) J. Immunol. Methods. vol. 150: 159–175.

NO ANTIGEN

MEDIUM / PLATE:PVDF 0.45

NO ANTIGEN

MEDIUM / PLATE:MAHA 0.45

ANTIGEN

TETANUS TOXOID / PLATE:PVDF 0.45

NO ANTIGEN

TETANUS TOXOID / PLATE:MAHA 0.45

TRANSLATOR WITH STOP

MICROSCOPE LENS

CUSTOM RING ILLUMINATOR ADJUSTOR

4R9 (Th1) 200 CELLS, IFNγ ASSAY

4R9 (Th1) 50 CELLS, IFNγ ASSAY

M33 (Th1) 200 CELLS, IFNγ ASSAY

M33 ((Th2) 200 CELLS, IL-5 ASSAY

M33 (Th2) 50 CELLS, IL-5 ASSAY

2-COLOR IFNγ & IL-5 ASSAY
4R9 & M33, 50 CELLS EACH

4R9 ((Th1) 200 CELLS, IL-5 ASSAY

DETECTING ALLOREACTIVITY

FIELD OF THE INVENTION

The present invention relates to devices and methods for detecting secreted cellular products, and in particular for measuring secreted T cell products, including cytokines.

BACKGROUND

Over the last thirty years, the immune system has been studied with better and better laboratory tools. Still, most knowledge of the immune response concerns antibody formation. This is understandable given that antibodies, including specific antibodies, are easily detectable in quantity in the serum of immunized individuals. Antibodies are products of B lymphocytes. Antibody production by individual B cells (as well as cells fused with B cells such as hybridomas) is also readily achieved in vitro using a variety of tests, including the ELISA spot assay (also called "ELISPOT" for "enzyme-linked immunospot"). See Segwick, J. D. and Holt, P. G., "A solid-Phase Immunoenzymatic Technique for the Enumeration of Specific Antibody-Secreting Cells," J. Immunol. Methods 57:301–309 (1983). See also Mazer, B. D. et al., "An ELISA Spot Assay for Quantitation of Human Immunoglobulin Secreting Cells," J. Allergy Clin. Immunol. 88:235–243 (1991).

In the conventional B cell ELISA spot assay, standard, commercially-available flat-bottom plates (containing no membranes) are coated overnight with antigen or animal antibody. In the case where antibody is used, it is typically an "anti-antibody" (e.g., goat antibody reactive with human IgG, IgE, IgM etc.). After blocking overnight, B cells are introduced in the wells. Following a sufficient culture period, the wells are washed free of the cells and an antibody-enzyme conjugate is added. The plates are then developed using substrate for the enzyme of the conjugate. Spots are counted using a microscope. The lowest amount of detectable antibody is typically in the range of 10 to 50 picograms. See e.g., Renz, H. et al., "Enhancement of IgE Production by Anti-CD40 Antibody in Atopic Dermatitis," J. Allergy Clin. Immunol. 93:658–668 (1994).

In contrast to the antibody response, the response of T cells to antigen (including the antigen of pathogens) can not be easily monitored due to the fact that antigen reactive T cells occur in low frequencies and the fact that their secretory products are not typically stable (i.e. have a short half-life). Indeed, even in hyper-immunized individuals, antigen reactive T cells constitute 1 in 10,000 cells or less in the peripheral T cell pool, e.g., among the T cells in circulating blood. Thus, T cells usually act beyond the detection limits of conventional assay systems (such as proliferation assays).

As a consequence of this, there is no technique at present available that would reliably measure whether a patient has generated a T cell response to a particular pathogen, such as HIV. There is no reliable assay that can detect whether a T cell response to HIV proteins has been generated, what proteins of the virus are primarily targeted, and which determinants within that protein are immunodominant. There is also no reliable method available for testing the magnitude of the anti-viral T cell response (clonal sizes) and its quality (e.g. whether the response is pro- or anti-inflammatory).

The heterogeneity of T cells, their products and the mode of function provide great challenges (particularly as compared to B cells). With respect to mode of function, T cells can act in different subpopulations that utilize strikingly different effector functions. T cell responses can be pro-inflammatory T helper 1 type, Th1, characterized by the secretion of interferon gamma (IFN$\gamma$) and interleukin 2 (IL-2). Th1 cells are critical for the cellular defense and provide little help for antibody secretion. (Strong Th1 responses are usually associated with poor antibody production, which highlights the importance of directly measuring the T cell response instead of relying on antibody measurements.) The other class of T cell responses is anti-inflammatory, mediated by Th2 cells that produce IL-4, 5, 10, but no IL-2 or IFN$\gamma$. Th2 cells are the helper cells for antibody production. $CD4^+$ and $CD8^+$ cells both occur in these subpopulations: Th1/Th2:CD4, TC1/TC2:CD8.

Importantly, for each type of infection there is an "appropriate" (and different) type of T cell response (e.g., Th1 vs. Th2, $CD4^+$ vs. $CD8^+$) that clears the infectious agent but does not cause excessive tissue destruction to the host. It is detrimental to the host if an "inappropriate" type of T cell response is engaged (Th1 instead of Th2, or vice versa). Thus, there is a strong need for assessing the host's T cell immunity to the virus to understand the host-virus interplay and to design vaccines. An ideal assay should permit monitoring all of the critical features of the T cell response: first, the existence of a response, i.e., that effector cells have been generated, second the nature of the effector cells as Th1 or Th2 type cells, and finally the magnitude of the response.

Some attempts have been made to apply the B-cell ELISA spot technology to T cells. However, the conventional cytokine ELISA spot assay has not been a more sensitive tool than alternative assays (e.g. proliferation assays), displaying high background and generally a weak signal. The conventional ELISA spot assay for T cells involves plates containing nitrocellulose membranes which are precoated with a capture antibody specific for the cytokine to be detected. See e.g., Taguchi, T. et al., "Detection of Individual Mouse Splenic T Cells Producing IFN$\gamma$ and IL-5 Using the Enzyme-Linked Immunospot (ELISPOT) Assay," J. Immunol. Methods 128:65–73 (1990). See also Fujihashi, F. et al., "Cytokine-Specific ELISPOT Assay," J. Imnmunol. Methods 160:181–189 (1993). See also Miyahira, Y. et al., "Quantification of Antigen Specific $CD8^+$ T Cells Using an ELISPOT Assay," J. Immunol. Methods 181:45–54 (1995). T cells are plated with the test antigen and start to secrete the type of cytokine they are programmed to produce. As the cytokine is released, it is captured around the secreting cells by the plate bound antibody. After 24h the cell culture is terminated, cells are removed and the plate bound cytokine is visualized by a second antibody and an enzymatic color reaction.

Ideally, each cytokine producing cell will be represented as an ELISA spot. However, with conventional assays, sensitivity does not exceed cytokine measurements in the supernatant by ELISA (cytokine measurements in culture supernatants provide a positive result only if more than 1000 cells are present per well). The quantification of the data is also problematic because of background problems and the subjective, visual evaluation.

There is a great need for better assays to measure secreted T cell cytokines. Specifically, there is a need for devices and methods with greater capability to detect cytokines from individual cells in a mixture of heterogeneous cells.

SUMMARY OF THE INVENTION

The present invention relates to devices and methods for detecting cellular products, and in particular for measuring secreted T cell products, including cytokines. The present invention contemplates a device and method comprising a membrane. In one embodiment, the membranes of the present invention are weakly hydrophilic and display advancing contact angles for water between approximately seventy (70) and approximately ninety (90) degrees. In another embodiment, the membranes of the present invention are hydrophobic and display advancing contact angles for water between approximately ninety (90) and approximately one hundred and thirty (130) degrees. In another embodiment, the membranes of the present invention are very hydrophobic and display advancing contact angles for water greater than approximately one hundred and thirty (130) degrees.

In accordance with one embodiment of the invention, the microwells containing the hydrophobic membrane of the present invention are precoated with a first capture reagent (see FIG. 1A). It is not intended that the present invention be limited by the nature of the capture reagent. In one embodiment, the capture reagent is a cytokine binding ligand such as a capture antibody specific for the cytokine to be detected (e.g., anti-IFNγ mAb1 or anti-IL5 mAb or with both simultaneously for the two color assay). In a preferred method, freshly isolated, primary cell populations (e.g., lymph node, spleen cells, etc.) are subsequently plated (see FIG. 1B) with the test antigen, e.g., HIV protein or peptide; control cultures contain irrelevant antigens or peptides. Since the primary cell suspensions contain abundant antigen presenting cells (APC) to process and present the antigen, specific T cells become activated and start to secrete the type of cytokine they are programmed to produce. As the cytokine is released, it is captured around the secreting cells by the plate-bound capture reagent (see FIG. 1B). After a suitable culture period (e.g., between approximately 30 minutes and 48 hours), the cell culture is terminated and the cells are removed (e.g. by washing), leaving the captured, plate-bound secreted product (see FIG. 1C).

The plate-bound, captured cytokine is visualized by a detection reagent. It is not intended that the present invention be limited by the nature of the detection reagent. In one embodiment, the detection reagent is a second cytokine binding ligand (e.g., antibody) free in solution that is conjugated to enzyme (see FIG. 1D). In another embodiment, the present invention contemplates the use of directly labelled detection reagents (e.g. antibodies). The addition of substrate (see FIG. 1E) results in an enzymatic color reaction. Each cytokine producing cell will be represented as an ELISA spot.

In still another embodiment, the detection reagents is directly labelled with a fluorochrome (e.g., FITC, PE or texas red) or with colored beads (different colors for different secretory products) or a ligand like biotin that can be detected with tertiary reagent that is labelled as above (with a fluorochrome, bead or enzyme).

While one embodiment of the present invention employs, as a first capture reagent, cytokine binding antibodies bound to a hydrophobic membrane to capture cytokines, the present invention also contemplates the binding of soluble products directly to the membrane without the use of capture reagents. In still another embodiment, the present invention contemplates non-antibody ligands, such as cytokine receptors and lectins (e.g. concanavalin A), as the capture ligand.

The present invention contemplates a testing device comprising: a plurality of microwells, a membrane within each of said microwells, wherein said membrane displays advancing contact angles for water greater than approximately seventy degrees, and a first cytokine binding ligand bound to said membrane. In one embodiment, said membrane displays advancing contact angles for water between approximately ninety (90) and approximately one hundred and thirty (130) degrees. In another embodiment, said membrane displays advancing contact angles for water greater than approximately one hundred and thirty (130) degrees. In a preferred embodiment, said membrane is a hydrophobic, PVDF-based membrane or a hydrophobic, nylon-based membrane. In yet another embodiment, the present invention contemplates a device having two membranes (for example, a first PVDF-based membrane and a second polypropylene membrane).

The present invention contemplates a variety of first cytokine binding ligands, including antibody specific for a cytokine (e.g. antibody specific for an interferon such as interferon gamma or antibody specific for an interleukin, such as IL-5) as well as cytokine receptors (e.g. interleukin receptors). Where more than one cell product is to be detected, the present invention contemplates a second cytokine binding ligand bound to said membrane.

In a specific embodiment, the present invention contemplates, a method of detecting secreted T cell cytokines, comprising: a) providing: i) a microwell comprising a hydrophobic membrane having a first cytokine binding ligand; ii) a primary cell population comprising T cells capable of secreting cytokines; b) adding said primary cell population to said microwell under conditions such that said T cell secretes a cytokine that binds to said first cytokine binding ligand; and c) detecting said secreted T cell cytokine. The present invention further contemplates an embodiment wherein said microwell further comprises, prior to said adding of step (b), a test antigen (such as a peptide).

The present invention is not limited by the nature of the primary cell population In one embodiment, the primary cell population further comprises antigen presenting cells.

In one embodiment, the present invention provides a method of detecting T cell cytokines, comprising: a) providing: i) a reaction chamber; ii) a hydrophobic membrane having a first cytokine binding ligand; iii) a first sample of cells obtained from a first human comprising T cells capable of secreting cytokines; and iv) a second sample of cells obtained from a second human comprising T cells rendered substantially incapable of secreting cytokines; b) adding said first and second samples to said reaction chamber to create a mixture; c) exposing said mixture to said hydrophobic membrane under conditions such that said first sample T cells secrete a cytokine that binds to said first cytokine binding ligand; and d) detecting said secreted T cell cytokine.

It is not intended that the present invention be limited by the nature of the reaction chamber. It is preferred that the chamber allow for culturing of the cells. Suitable cell culturing means include, but are not limited to, tissue culture plates, microtiter plates, and test tubes. It is preferred that said mixture of cells is incubated prior to exposing the mixture to said hydrophobic membrane. Moreover, it is preferred that said mixture of cells is removed from said reaction chamber or tissue culture means following incubation and washed in cell culture media (or other buffered media) prior to said exposing to said hydrophobic membrane.

It is not intended that the present invention be limited by the nature of the treatment by which said second sample T cells are rendered substantially incapable of secreting cytokines. Said second sample T cells may be, for example, irradiated. On the other hand, such T cells may be rendered substantially incapable of secreting cytokines by exposure to chemical substances. By "substantially incapable" it is meant that the normal capability is impaired and secretion, if any, is minimal (i.e. is reduced to approximately background levels).

The present invention contemplates a variety of detecting schemes. In one embodiment, said detecting comprises introducing a second cytokine binding ligand into said microwell under conditions such that a colorimetric signal is generated.

The present invention contemplates computer image analysis. In one embodiment, the analysis method detects and categorizes spots on a membrane, and comprises: a ) providing a testing device, comprising i) a plurality of microwells, and ii) a membrane (such as a hydrophobic membrane) within each of said microwells, wherein said membrane has been treated under conditions such that spots could develop; b) capturing an image of each of said membranes from each of said microwells; c) digitizing said images to create digitized images comprising bits; and d) thresholding said digitized images, such that said spots on said membranes are detected and categorized. Said thresholding may comprise superimposing an inverted binary bit map of a predetermined threshold on each of said digitized images and eliminating those bits not meeting the threshold.

DESCRIPTION OF THE DRAWINGS

FIG. 1 schematically shows one embodiment of the method of the present invention.

DESCRIPTION OF THE INVENTION

Figure 1A:
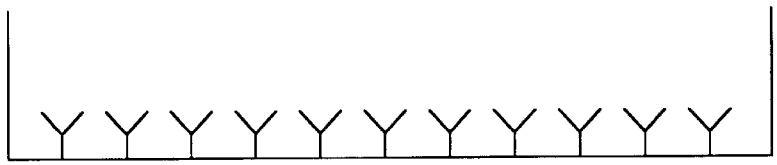
FIG. 1A shows a capture reagent ("Y") bound to a hydrophobic membrane within a test well.

The present invention relates to devices and methods for detecting cellular products, and in particular for measuring secreted T cell products, including cytokines. T cells are recognized as mediating the first line of defense against intracellular pathogens, such as viruses. An ever-increasing number of viruses are being identified as the source of human disease. The better known diseases caused by viruses include influenza, hepatitis, poliomyelitis, rabies, and now, of course, the human immunodeficiency virus (HIV) of Acquired Immunodeficiency Syndrome (AIDS). The cytokine ELISA spot system of the present invention holds the promise to permit, for the first time, direct monitoring of the T cell response to viruses, such as HIV.

The ELISA spot assay of the present invention involves microplates containing membranes displaying virtually no background, a considerable achievement over the conventional assays using conventional membranes. The membranes of the present invention are "hydrophobic."

One skilled in the membrane art recognizes there are a number of methods for determining the hydrophobicity of membranes. One method involves measuring the contact angles of liquids. While it is not intended that the present invention be limited by the nature of the particular mechanism or the understanding of the particular physical forces involved, a drop of liquid resting on the surface of a membrane may be considered to be balancing three forces: a) the interfacial tension between the solid and liquid, b) the interfacial tension between the solid and vapor, and c) the interfacial tension between the liquid and the vapor. The angle within the liquid phase is known as the "contact angle" or "wetting angle." See B. C. Nayar and A. W. Adamson, "Contact Angle in Industry" Science Reporter, pp. 76–79 (February 1981). It is the angle included between the tangent lane to the surface of the liquid and the tangent plane to the surface of the solid at an point along their line of contact.

Advancing and receding contact angles are frequently found not to be the same. This hysteresis may be due to rough surfaces on the membrane or other artifacts (e.g. contamination of the liquid being tested). It is common practice to measure and report advancing contact angles.

One method of measuring the contact angle is by taking a photograph of the sessile drop resting on the membrane and then measuring the angle from the print. The angle can also be measured from an enlarged image of the drop. A low power microscope produces a sharply defined image of the liquid drop which is observed through the eyepiece as a silhouette.

There are commercially available goniometers with environmental chambers in which contact angles can be determined in controlled conditions of temperature and pressure. A camera can also be attached to such goniometers. Commercial instruments for measuring contact angles are available from such companies as RAME-HART, Inc. (Mountain Lakes, N.J.), KRUSS (Charlotte, N.C.), CAHN INSTRUMENTS (Cerritos, Calif.), and KERNCO INSTRUMENTS (El Paso, Tex.).

The angle ranges from zero (0) to one hundred and eighty (180) degrees (although the latter is not encountered in practice). Where water on a membrane displays a contact angle between approximately zero and approximately ninety (90) degrees, the membrane is considered hydrophilic. Ninety (90) degrees is considered "hydroneutral." Where water on a membrane displays a contact angle greater than ninety (90) degrees, the membrane is considered hydrophobic. Where the contact angle is greater than approximately one hundred and thirty (130) degrees the membrane is considered extremely hydrophobic. In one embodiment, the membranes of the present invention are weakly hydrophilic and display advancing contact angles for water between approximately seventy (70) and approximately ninety (90) degrees. In another embodiment, the membranes of the present invention are hydrophobic and display advancing contact angles for water between approximately ninety (90) and approximately one hundred and thirty (130) degrees. In another embodiment, the membranes of the present invention are very hydrophobic and display advancing contact angles for water greater than approximately one hundred and thirty (130) degrees.

A preferred hydrophobic membrane of the present invention is nylon or polyvinylidene difluoride "PVDF" polymer-based and is available commercially from Gelman Sciences Membrane and Device Division (Ann Arbor, Mich.). Plates containing PVDF membranes are available commercially from Polyfiltronics (Rockland, Mass.). As a membrane, the pore size is generally greater than 0.1 microns and less than 1.0 microns, and preferably approximately 0.45 microns. Such PVDF-based membranes are "depth membranes" and increase the sensitivity of the assay more that 10 fold and dramatically reduce the nonspecific background.

Other depth membranes are available commercially (e.g. PVDC, nylon, etc.). While it is not intended that the present invention be limited by the nature of the particular mechanism or the understanding of the particular physical forces involved, it is believed that molecules are captured within thin the interstices of a depth membrane, providing a high binding capacity and large surface area. Such membranes can be treated such that they are hydrophobic (e.g. a hydrophobic, nylon-based membrane).

The hydrophobic membranes of the present invention provide a barrier to aqueous liquids. Because of the membrane's hydrophobicity, the membrane will block the flow of liquid under the conditions used for the practice of the invention. This type of "liquid barrier" membrane design has been found to have benefits compared to the "flow through" membrane-containing plates available from Millipore Corporation (Marlborough, Mass.). Moreover, the nitrocellulose membranes typically sold display advancing contact angles for water less than approximately seventy degrees and more typically less than approximately sixty degrees.

Microtiter plates or "microplates" were introduced in the 1960's to facilitate laboratory testing in situations where a large number of tests were run simultaneously. The most typical microplates contain ninety-six (96) molded plastic wells (in an 8×12 array) with a typical sample volume capacity of about 0.2 milliliters. It is not intended that the assays of the present invention be carried out in a particular plate format; a range (e.g. approximately 0.010 to 0.200 milliliters, and preferably 0.050 milliliters) is contemplated.

A wide variety of mechanical fluid handling devices are now available so that specimens, chemical solutions and other liquids can be transferred into the wells of microplates. Usually a row of eight (8) or twelve (12) wells are filled simultaneously, but some handling devices can simultaneously add sample to all of the wells. It is not intended that the present invention be limited to microplates made of particular materials, or to microwells of particular dimensions or volumes. In one embodiment, the microplate is made of hard plastic such a polystyrene.

The preferred plate is a plate that is not completely transparent. Transparent plates conduct and refract the light in highly irregular patterns, creating problematic variations in illumination of the membrane. There is also a problem with the highly polished and thereby reflective nature of the interior sides of the wells, which creates distorted mirror images of the spots during analysis, as well as compounding the variations in the lighting.

The preferred plate of the present invention is made from a white, translucent version of the same plastic (not ivory, or any other tint that would introduce color to the light). The vertical walls of the wells are treated (e.g. with sandpaper) so as to achieve a matte or slightly roughened finish, thereby avoiding interior mirror reflections. In selecting the plastic, it is important that it be suitable in tissue culture (i.e., suitable in the sense that the cells do not adhere to the walls, rather than the membrane) and are not toxic. With this embodiment, it is preferred that the top surface of the plate be made non-reflective so that there is no interference with the image analysis. This can be done, for example, by painting the surface with non-reflective black paint to create a black mask.

In one embodiment, the present invention contemplates a 96-well microtiter plate comprising a hydrophobic membrane attached to the perimeter or periphery of each well and enclosed by a solid bottom. This embodiment can be made using a two-plate assembly approach. In this case, the "A plate" has the membrane attached to the periphery of each well. This "A plate" is bonded to a "B plate" which encloses the bottom, i.e., with solid plastic under the membrane.

The membrane may be attached to the microwells by any number of conventional technologies including: adhesive attachment, heat sealing, solvent sealing, chemical bonding and ultrasonic welding. Ultrasonic welding is a preferred method of attaching the PVDF membrane to the periphery of the microwells of the present invention. Ultrasonic welding is described in U.S. Pat. Nos. 4,948,442 and 5,047,215 to Roy Manns, hereby incorporated by reference.

The Use of Multiple Membranes

The use of a single membrane filtration method may result in leakage when the assay plates have been subjected to low temperature after manufacturing (for example, during shipping in the winter months). While the precise mechanism is not known, it is believed that leakage occurs when the seal around the periphery of the plate wells become compromised through contraction and expansion. The resulting leakage leads to ambiguity and confusion when interpreting assay results.

The present invention therefore contemplates a multiple membrane device, and more particularly, a double membrane microtitre plate assemblage to minimize, if not eliminate, the problem of leakage caused by exposure to low temperatures. In one embodiment of the double membrane design of present invention, the device comprises A and B microtiter plates, a hydrophobic membrane and a filtration means, generally a filtering membrane, located between the plates.

The A plate for the double membrane device is formed with a plurality of identical wells, each extending from one respective opening in one substantially planar surface to another respective opening in the opposed planar surface of the plate. The volume of the well is determined by the thickness of the plate as well as the diameter and the shape of the well. The diameter of the wells is determined by their number and spacing within the plate. The plurality of wells arranged in a 12×8 regular rectangular array spaced about 0.9 cm. center-to-center is an example of typical well spacing. The shape of the wells may be cylindrical, conical or have other configurations depending upon the wishes of the designer or user. In one embodiment, each opening in the "underneath interface surface" of the culture plate is circumscribed with a groove or channel. The circumscribing structure may be a circle or it may take other geometrical shapes such as squares and the like. The term "underneath interface surface" used above refers to the substantially planar surface of the A plate that will interface with the B plate.

The B plate is preferably substantially planar, substantially rigid, water-insoluble, fluid impervious, thermoplastic material. The plate material is chemically nonreactive with the fluids to be employed in the assays to be carried out with the apparatus. The term "substantially rigid" as used here is intended to mean material that will resist deformation or warping of the substantially planar surface when the plate is subjected to light mechanical or thermal stress.

While it is not intended that the present invention be limited by the specific material for the A and B plates, the preferred material is a polystyrene, for it provides very low, non-specific protein binding, making it specially suitable for use with samples, such as peripheral blood mononuclear cells.

The B plate is also a rectangular body having at least one substantially planar surface. The substantially planar "upper interface surface" will interface with the A plate upon final assembly. The B plate is provided with a plurality of apertures extending from the upper interface surface of the plate. The apertures are the same in number, arrangement and spacing as the wells of the A plate so that the apertures can register with the openings of the culture plate at the underneath interface surface when the upper interface surface of the B plate is adjacent and parallel to the underneath interface surface of the A plate. In one embodiment, each aperture of the B plate is circumscribed at the upper interface surface with an upstanding ridge. The geometric shape of each aperture should match that of the channel or groove found on the underneath interface surface of the A plate and the width of the ridge should be small enough to permit the ridge to mate with the channel or groove of the B plate when the plates are suitably positioned and pressed together.

It should be clear that the present invention is not limited by which plate contains the channels or grooves and which one contains the ridges. The requirement for functionality is that each of the two plates contain a compatible structure which can be aligned to form a seal between the plates.

The double membrane micro-titre plates are assembled by fitting the A plate into the B plate with the underneath and upper interface surfaces facing one another, and two membranes placed between the interface surfaces. The plates are arranged so that each opening at the bottom of each well found on the underneath interface surface of the culture plate is registered with a corresponding opening of the aperture found on the upper interface surface of the harvester plate. Further, each ridge on the upper interface surface of the harvester plate is thus mated with a corresponding channel or grove found on the underneath interface surface of the culture plate.

The assemblage is then subjected to uniformly distributed pressure directed to the planes of the interfacing surfaces of the culture and harvesting plates. The pressure is sufficient in magnitude to force the top edges of ridges into close contact with the interior surface of channels or grooves, severing the membrane at the outer edge of the ridge and crushing that portion of the membranes trapped between the ridges and channels.

Preferably, the first membrane is PVDF-hydrophobic and the second membrane is melt blown polypropylene mesh (with an average pore size of approximately 1–5 microns, and more preferably 1–2 microns). There are a number of advantages to the arrangement where the second membrane supports the PVDF membrane. First, it should be noted that the PVDF membrane, when used alone, can be fragile and tends to sag; when the PVDH membrane is used with a second membrane, however, the PVDF membrane is rigid and flat due to mechanical stabilization. Second, the use of a second membrane allows for less leakage caused by surfactants, such as Tween; provided the concentration of surfactants is kept relatively low and the time of exposure to such surfactants is relatively brief, leakage is minimized.

The double membrane design described above is superior to the single membrane design in that the single membrane assemblage has been found to leak when subjected to reduced temperatures. The double membrane assemblage appears to be better suited to withstanding low temperatures after manufacturing.

Detection of Cell Products, Including Cytokines

With the hydrophobic membranes of the present invention one can obtain very clear signals (which are readily suited for image analysis) where previously signals (using conventional nitrocellulose based designs) were ambiguous or not detectable at all. One can detect a single cytokine producing cell with the improved microtiter plates of the present invention. Indeed, the microtiter plates of the present invention represent a major development in lowering the detection limit for monitoring T cell responses.

While particularly suitable for measuring T cell products such as cytokines, it is also not intended that the invention be limited to the type of sample. The present invention can be employed with success with all types of liquid samples, including various different suspensions of biological material.

In accordance with one embodiment of the invention, the microwells containing the hydrophobic membrane of the present invention are precoated with a first capture reagent (see FIG. 1A). It is not intended that the present invention be limited by the nature of the capture reagent. In one embodiment, the capture reagent is a cytokine binding ligand such as a capture antibody specific for the cytokine to be detected (e.g., anti-IFNγ mAb1 or anti-IL5 mAb or with both simultaneously for the two color assay). In a preferred method, freshly isolated, primary cell populations

TABLE 1

| Name | Abbr. | Type | Specific Name |
|---|---|---|---|
| Interferons | IFN | alpha | Leukocyte Interferon |
| | | beta | Fibroblast Interferon |
| | | gamma | Macrophage Activation Factor |
| Interleukins | IL-1 | 1 alpha | Endogenous Pyrogen |
| | | 1 beta | Lymphocyte-Activating Factor |
| | | 1 ra | IL-1 Receptor Antagonist |
| | IL-2 | | T-cell Growth Factor |
| | IL-3 | | Mast Cell Growth Factor |
| | IL-4 | | B-cell Growth Factor |
| | IL-5 | | Eosinophil Differentiation Factor |
| | IL-6 | | Hybridoma Growth Factor |
| | IL-7 | | Lymphopoietin |
| | IL-8 | | Granulocyte Chemotactic Protein |
| | IL-9 | | Megakaryoblast Growth Factor |
| | IL-10 | | Cytokine Synthesis Inhibitor Factor |
| | IL-11 | | Stromal Cell-Derived Cytokine |
| | IL-12 | | Natural Killer Cell Stimulatory Factor |

TABLE 1-continued

| Name | Abbr. | Type | Specific Name |
|---|---|---|---|
| Tumor Necrosis Factors | TNF | alpha | Cachectin |
| | | beta | Lymphotoxin |
| Colony Stimulating Factors | CSF | GM-CSF | Granulocyte-macrophage Colony-Stimulating Factor |
| | | Mp-CSF | Macrophage Growth Factor |
| | | G-CSF | Granulocyte Colony-stimulating Factor |
| | | EPO | Erythropoietin |
| Transforming Growth Factor | TGF | beta 1 | Cartilage-inducing Factor |
| | | beta 2 | Epstein-Barr Virus-inducing Factor |
| | | beta 3 | Tissue-derived Growth Factor |
| Other Growth Factors | LIF | | Leukemia Inhibitory Factor |
| | MIF | | Macrophage Migration-inhibiting Factor |
| | MCP | | Monocyte Chemoattractant Protein |
| | EGF | | Epidermal Growth Factor |
| | PDGF | | Platelet-derived Growth Factor |
| | FGF | alpha | Acidic Fibroblast Growth Factor |
| | | beta | Basic Fibroblast Growth Factor |
| | ILGF | | Insulin-like Growth Factor |
| | NGF | | Nerve Growth Factor |
| | BCGF | | B-cell growth factor |

Figure 1B:
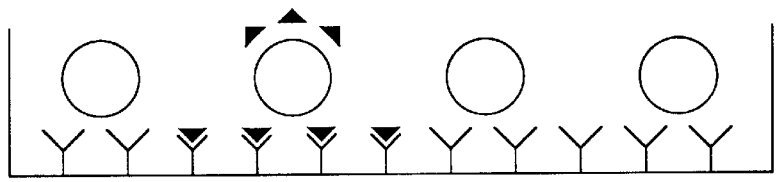
FIG. 1B shows cells in solution secreting soluble products (solid black diamonds) binding to the immobilized capture reagent.
Figure 1C:
FIG. 1C shows membrane bound secreted product.

(e.g., lymph node, spleen cells, etc.) are subsequently plated (see FIG. 1B) with the test antigen, e.g., HIV protein or peptide; control cultures contain irrelevant antigens or peptides. Since the primary cell suspensions contain abundant antigen presenting cells (APC) to process and present the antigen, specific T cells become activated and start to secrete the type of cytokine they are programmed to produce. As the cytokine is released, it is captured around the secreting cells by the plate-bound capture reagent (see FIG. 1B). After a suitable culture period (e.g., between approximately 30 minutes and 48 hours), the cell culture is terminated and the cells are removed (e.g. by washing), leaving the captured, plate-bound secreted product (see FIG. 1C).

Figure 1D:
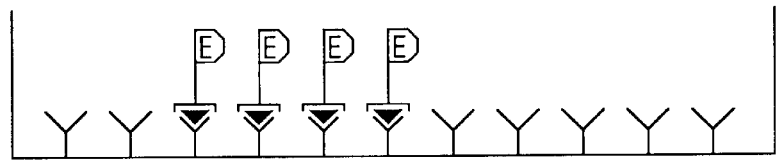
FIG. 1D shows binding of detection reagents ("_P_") containing enzyme ("E") after their addition free in solution.
Figure 1E:
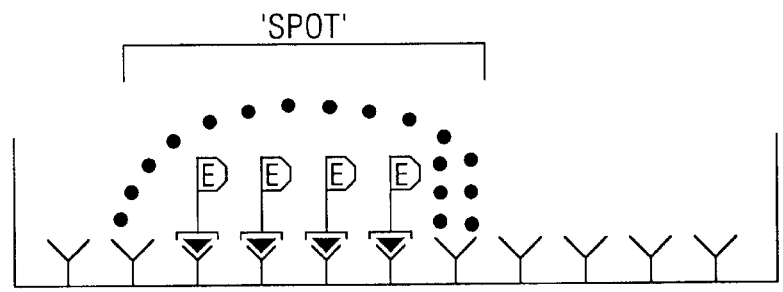
FIG. 1E shows precipitating substrate (solid black circles).
Figure 2A:
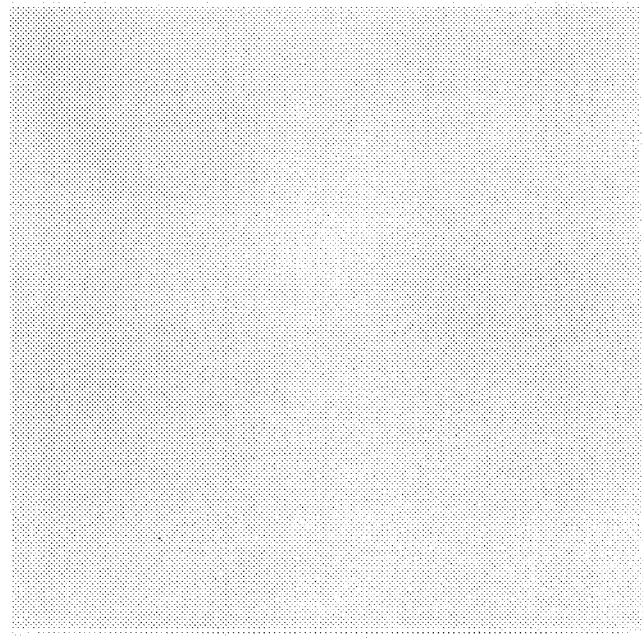
FIGS. 2A, 2B, 2C and 2D are photographs of results of ELISA spot assays comparing the microwells of the present invention, i.e., containing a hydrophobic membrane, with a conventional assay using a conventional membrane.
Figure 2B:
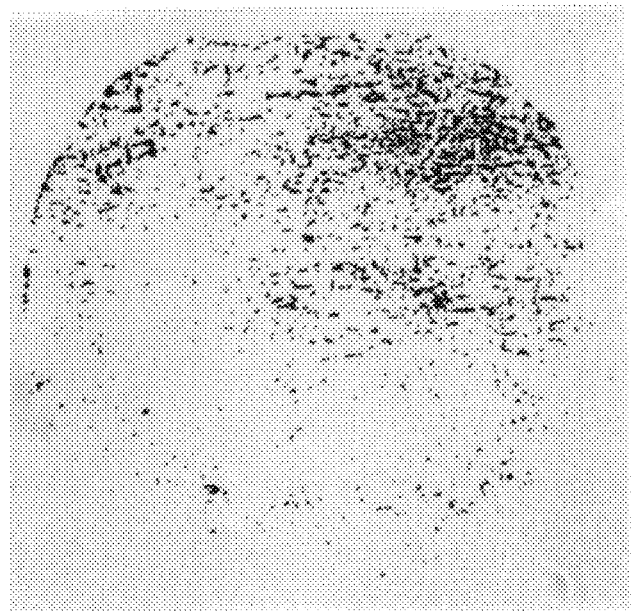
Figure 2C:
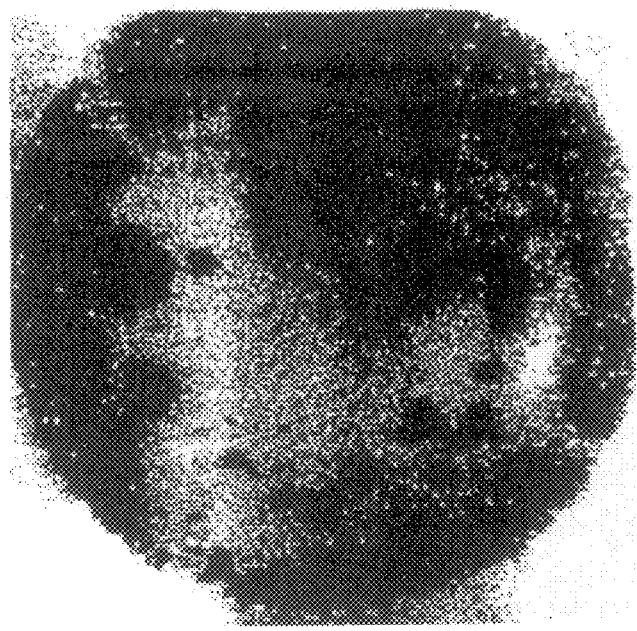
Figure 2D:
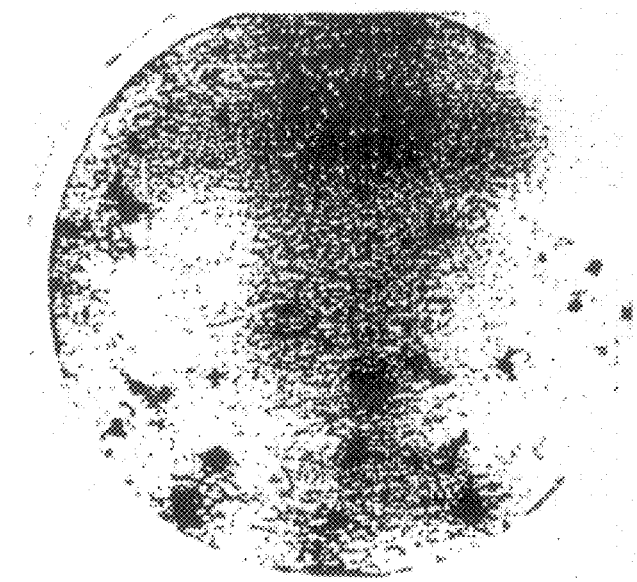

The plate-bound, captured cytokine is visualized by a detection reagent. It is not intended that the present invention be limited by the nature of the detection reagent. In one embodiment, the detection reagent is a second cytokine binding ligand (e.g., antibody) free in solution that is conjugated to enzyme (see FIG. 1D). The addition of substrate (see FIG. 1E) results in an enzymatic color reaction. Each cytokine producing cell will be represented as an ELISA spot.

It is not intended that the present invention be limited by the nature of the cytokine to be detected. Cytokines are hormone-like substances secreted by a wide variety of cells, including (but not limited to ) lymphocytes (e.g., T cells), macrophages, fibroblasts, and endothelial cells. It is now known that cytokines consist of a broad class of glycoproteins that have the ability to regulate intercellular communication (e.g., cell-cell interaction) in both normal and pathologic situations. Cytokines generally contain from approximately 60 to 200 amino acid residues, with a relative molecular weight of between 15 and 25 kd. At least 35 distinct cytokines have been elucidated (see Table 1 above).

There is also a family of chemoattractant cytokines known as "chemokines." See e.g. T. J. Schall and K. B. Bacon, "Chemokines, leukocyte trafficking, and inflammation" Curr. Op. Immun. 6:865–873 (1994). These molecules share structural similarities, including four conserved cysteine residues which form disulfide bonds in the tertiary structures of the proteins. The present invention contemplates employing the devices and methods of the present invention for detecting secreted chemokines.

While the invention is not limited by the nature of the particular cytokine, the role of many cytokines is now known. For example, interleukin-1 and interleukin-1B (IL-1α and IL-1B) are distantly related polypeptide hormones which play a central role in the regulation of immune and inflammatory responses. See D. P. Cerretti et al., U.S. Pat. Nos. 4,894,333 and 4,879,374, each hereby incorporated by reference. These two proteins were originally both classified as IL-1, based on a shared lymphocyte activation factor (LAF) activity, and a common major cellular source, activated macrophages. As information has accumulated from studies using purified natural and recombinant IL-1 molecules, it has become clear that IL-1α and IL-1B each mediate most, if not all, of the wide range of activities previously ascribed to IL-1.

TNF-α plays a critical role in the development of acute pulmonary failure and injury. When released into the lung, TNF-α has devastating effects, causing rapid and diffuse tissue injury. This is presumably a direct result of its known effects on endothelial cells and granulocytes, as well as its induction of other mediators such as IL-1, prostaglandins, and platelet-activating factor.

While one embodiment of the present invention employs, as a first capture reagent, cytokine binding antibodies bound to a PVDF-based membrane to capture cytokines, the present invention also contemplates the binding of soluble products directly to the membrane without the use of capture reagents. In still another embodiment, the present invention contemplates non-antibody ligands, such as cytokine receptors and lectins (e.g. concanavalin A), as the capture ligand.

With respect to cytokine receptors, the existence of IL-1 plasma membrane receptors which bind both IL-1α and IL-1B is now well-established. IL-1 receptors have now been cloned and expressed in high yield. See S. K. Dower, U.S. Pat. No. 4,968,607, hereby incorporated by reference. Similarly, tumor necrosis factor-α and B receptors have been isolated and DNA sequences encoding these secretory proteins are described. See C. A. Smith et al., European Patent Application No. 90309875.4 (Publication No. 0418014A1), hereby incorporated by reference. See also U.S. Pat. application Ser. Nos. 405,370, 421,417 and 523,635, hereby incorporated by reference.

The present invention also contemplates the use of the improved microtiter plates to detect and/or screen synthetic cytokine analogues and inhibitors. Cytokine analogues are those compounds which act in an analogous manner as the known cytokine. An example of such an analogue is described in European Patent Application No. 343684, hereby incorporated by reference. See also U.S. Pat. application Ser. Nos. 266,531, 199,915, 238,713, 248,521, and 238,171, hereby incorporated by reference. In that case, the analogue is a polypeptide inhibitor of interleukin-1.

Finally, the present invention can be used with success to measure a variety of cellular products other than cytokines. In one embodiment, the present invention contemplates detecting other products of T cells such as performs and granzymes. Perforin is a lytic protein and granzymes are a family of natural serine proteases; these products are stored in secretory granules until released from the cell. See e.g. G. Berke, "The CTL's Kiss of Death" Cell 81:9–12 (1995).

The present invention also contemplates measuring products from cells other than T cells. For example, the device and method of the present invention can be employed to detect the expression and secretion of recombinant products from host cells.

DESCRIPTION OF THE PREFERRED EMBODIMENTS

The present invention relates to devices and methods for detecting cellular products, and in particular for measuring secreted T cell products, including cytokines. In one embodiment, the present invention contemplates using the ELISA spot assay of the present invention as a functional measurement of alloimmune responses, and in particular, as a measurement of potential allograft rejection in the field of human organ transplantation.

In this regard, it should be stressed that up to 30–40% of transplanted organs are lost over 5 years, mostly due to chronic rejection. Importantly, present HLA matching procedures are based on defining serological or structural differences between HLA alleles, but do not reveal any functional information regarding potential alloreactivity. Detectable single amino acid differences between HLA alleles may, or may not, be clinically important. There is thus a clear need for improved techniques that can provide predictive functional information above and beyond the present typing technologies.

The present state of clinical organ transplantation requires the use of immunosuppressive agents to prevent acute transplant rejection. The exact pharmacological regimen used for immunosuppression varies significantly from one transplant center to the next, but generally includes cyclosporine A, corticosteroids and azathioprine, in some combination. Serum or whole blood cyclosporine levels are used primarily to prevent toxicity and not to evaluate the level of immunosuppression; it is well established that patients with therapeutic cyclosporine levels can develop acute rejection episodes. Additionally, cyclosporine levels do not provide any information about the relative immunosuppressive effects of the other agents used in conjunction with the cyclosporine A. There is presently no method for assessing the immunosuppressive effects of corticosteroids or azathioprine (except to evaluate for signs of clinical toxicity), and medication doses are often adjusted empirically. Thus, as is the case with structural-based assays for tissue typing, there are presently no methods available to functionally assess the quality or quantity of the alloimmune response in transplant recipients.

The present invention can fill this need. It is contemplated that ELISA assay of the present invention will measure existing and potential human alloimmune responses by accurately detecting and quantifying allospecific cytokine profiles. The assay of the present invention has a number of advantages that make it ideal for the monitoring of T cell activity in vivo. Detection of the cytokine occurs directly at its source, i.e. the secreting cell, before it is diluted, degraded, or absorbed to receptors on a bystander cell, thus making it extremely sensitive. Indeed, the assay can detect single antigen-reactive cells. Secondly, the ELISA spot assay measures clonal sizes, defining the frequencies of antigen-reactive, or alloreactive T cells in the bulk population. Since the 24 hour duration of the assay is too short for T cell proliferation to occur in vitro, the frequency of detected T cells is reflective of the in vivo frequency. Thirdly, the assay identifies the cytokine profile of each responding cell. This approach is additionally superior to previously published, time consuming, isolation and characterization of in vitro cultured T cell clones, in that the short incubation time of the ELISA spot assay circumvents in vitro artifacts.

The assay of the present invention is very sensitive. This improved sensitivity is central to monitoring alloreactivity in a potentially infrequent responding population: immunosuppressed transplant recipients. The sensitivity is also central to detecting responses between related and unrelated individuals. By "related" individuals (such as humans) it is meant that such individuals have a common ancestry (e.g. children of the same parents, cousins, etc.). By "unrelated" individuals it is meant that such individuals have no known ancestral relationship.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); BD (Becton Dickenson, Bedford Mass.); ENDO (Endogen, Cambridge, Mass.); PHRM (Pharmingen, San Diego Calif.).

In considering the automated imaging method of the present invention, some definitions are helpful. For example, when saving an image, it can be saved in varying degrees of resolution and with varying numbers of colors; a 24 bit image is three times larger than an 8-bit image and includes a sharper image and more colors. When "adding an image" is specified, this means to add the pixel values of corresponding pixels to each other. As used herein, "adjusting a light setting" means increasing or decreasing the light setting depending on the initial luminance of the different wells. A "bitmap" is a binary image consisting of only black and white pixels, such as is created after a thresholding process. A "buffer" is a location for temporarily storing data. A "corrected image" is the image formed after a specific filtering or smoothing process is performed on the image. As used herein, "filtering the image" means removing any noise or extraneous information from an image (in most instances, it sharpens the image for a more accurate reading of the image). As used herein, "extracting an average luminance" is where a single luminance value of a well is obtained by averaging the intensity levels of the pixels in the image. As used herein, "creating areas in an image for inspection" means isolating connected sets of pixels that meet a given threshold in an image for review. When "imaging wells" is specified, this involves any means for generating an image of the wells, such as using a camera to create a digital image of the wells. As used herein "loading an image into a location" means placing said image in said location. When "processing images" is specified, this involves those steps performed on the captured images, including but are not limited to filtering the image, enhancing the image, and locating and categorizing the spots. When "sorting areas" is specified, this involves categorizing objects in extracted areas which fall within predetermined parameters; these parameters indicate what the objects represent. As used herein, "smoothing the background" means eliminating large scale variations in lighting and coloration caused by uneven lighting or other irregularities in the membrane of the well. As used herein, "thresholding" means the process of comparing each pixel in an image to a set of values for Red-Green-Blue color layers from which a new image or bitmap can be created. When "watershed filtration" is specified, this allows for identification of objects in an image of widely differing luminances. A "Proof Sheet" is a single image made up of numerous smaller images of different wells. This is the similar to a proof sheet in photography. Finally, "incrementing" means to increase a value by one and "decrementing" means to decrease a value by one.

EXAMPLE 1

Use of Hydrophobic Membrane In ELISA SPOT Assay

In this example, a hydrophobic membrane is employed in a microtiter plate to detect cellular products. First, a hydrophobic membrane is coated with anti-interferon β (IFNα antibody 1) as the capture reagent. After several hours of incubation (2 hrs to overnight), during which the capture reagent(s) bind(s) to the membrane, excess reagent is washed away. The unsaturated surfaces of the membrane are then blocked with irrelevant protein (bovine serum albumin or gelatin) to prevent subsequent nonspecific binding of proteins. Following the blocking step, the plates are washed to remove non-plate bound, excess blocking reagent.

At this point the membrane is properly prepared to test cells. In this case, human peripheral blood mononuclear lymphocytes (PBL) are added at a concentration of ~$5\times10^5$ per well. Specific antigen (e.g. HIV antigen) is added to the experimental wells, control wells contain no antigen or irrelevant antigen (e.g. myohemerythrin, a protein that humans have not encountered). Among all cells plated (~$5\times10^5$ cells) only the antigen specific T cells will be stimulated by the antigen to release secretory products (e.g. IFNγ). In the control wells, in the absence of the antigen, antigen specific cells are not stimulated and do not release secretory products. During a 4–48 hr cell culture period (dependent on the product to be detected) the antigen specific cells secrete their products(s) being captured by the capture reagents around the secreting cell.

Following the culture period, the cells are washed away, leaving their secretory product retained on the membrane. A detection reagent is added to bind to the plate-bound secretory product (the detection and capture antibodies specific for secretory products, e.g., IFNγ have to recognize different parts of the molecule such as not to interfere with each other's binding). The detection reagents is/are either directly labelled with a fluorochrome (e.g., FITC, PE or texas red) or with colored beads (different colors for different secretory products) or enzymes whose substrates can give different color reactions (e.g., horseradish peroxidase, HRP, or alkaline phosphatase, ALPH) or a ligand like biotin that can be detected with tertiary reagent that is labelled as above (with fluorochrome, bead or enzyme). Directly labelled detection antibodies are preferred. Alternatively, labelled antibody is added that is specific for the unlabelled secondary reagent. In this case, HRP conjugated anti-IFNγ detection antibody is added. After an incubation period, excess detection reagent is washed away.

The present invention contemplates a variety of means for visualizing the detection reagent such as: a) immune fluorescence if the secondary (or tertiary) reagent was a fluorochrome, b) colored beads (different colors for different secretory products) visualized by light microscopy, c) or enzymatic reactions whose products generate a colored precipitate. In this case, 3-amino-9-ethylcarbazole ("AEC" commercially available from Pierce) is used. HRP activated AEC gives a red product that can be seen by light microscopy. Each "spot" of colored substrate corresponds to one cell secreting the product. The difference in number of spots between antigen stimulated wells and the number of spots in the negative control wells (with medium alone or irrelevant antigen) establishes the "signal" to be analyzed (usually there is no spot formation in the negative control). Sizes of the spots correspond to the quantity of product secreted, the number of spots establishes the frequency of antigen specific cells in the cell population tested (i.e. cells that were induced by the antigen to secrete the product among all cells plated, e.g., 20 IFNγ spots in HIV antigen challenged PBL represent a frequency of 40/million, if $5\times10^5$ cells were plated).

EXAMPLE 2

Comparison With Conventional Membranes

In this example, the microwells of the present invention, i.e., containing the PVDF-polymer based membranes, were compared with conventional nitrocellulose membranes used in ELISA spot assays. Peripheral blood mononuclear cells (PBL) of a tetanus toxoid (TT) immunized donor were plated at $2\times10^5$ cells per well in PVDF-based membrane-containing plates and nitrocellulose based plates ("MAHA" from Millipore). The microwells were tested with and without antigen (TT) (10 μg/ml). The membrane was coated (see Example 1) with antibody capable of detecting human interferon gamma (IFNγ) (antibody M-700A, commercially available from Endogen) at 5 ug/ml, overnight. Plates were then washed and the PBL were added at $3\times10^3$ cells per well. The cells were cultured in the plates for 48 h in an incubator and then removed by washing. Biotinylated second antibody, also specific for human IFNγ (M701, Endogen, 10 μg/ml) was added overnight and the plate bound second antibody was detected via the streptavidin/AEC reaction resulting in the red color reaction.

The production of the cytokine (see FIG. 2) was measured in the absence of the antigen (negative control, images on the left) and in the presence of the antigen, TT (test wells, on the right). The data show that the PVDF membrane-containing plates detect a clear specific signal in the experimental wells (top right) with virtually no background in the negative control (top left). In contrast, the specific signal is much weaker on nitrocellulose plates (bottom right) and there is considerable nonspecific background in the negative control (bottom left). Importantly, when tested in a conventional T cell proliferation assay when the culture supernatant is tested by a conventional IFNγELISA assay, barely significant results were obtained, which underlines the diagnostic potentials of the new plates. As is evident, the PVDF-modified membranes significantly increases the sensitivity of the assay while dramatically reducing the nonspecific background. With these new plates, it is possible to detect a single cytokine producing cell.

EXAMPLE 3

Automation And Quantitative Results

While the cytokine ELISA spot assay of the present invention can be visually evaluated, the exact quantification of the results is difficult and prone to subjective error. The present invention, therefore, contemplates evaluation of the data by using a computer image analysis system. In one embodiment (FIG. 3), a video camera (5) is mounted on the camera port of a dissection microscope (6) to capture an image of each microwell in a test plate (8) resting on a positioning platform (9). This information is sent to a digitizer and board based image analyzer in a computer (1) that employs a morphometric program; commercially available software (shown as item 4), including Windows, Optimas 5.2 and Excel 5.0 is used along with a VGA monitor (2)

with resolution at 640×480; in addition, software has been developed for particular applications and this is described in more detail below. The microscope (6) has a scanning stage (10) that is driven by control signals from the computer (1), which permits the sequential analysis of each of the 96 wells on the test plate (8), individually and fully automatically. The image analyzer, which can be viewed on a high resolution RGB monitor (3), is a highly developed system frequently used for histologic analysis which has been adopted for the present invention to isolate and identify spots meeting objective criteria for size, chromatic density, and shape. Importantly, absolute criteria are established to classify a spot which permits objective comparison of separate wells and assays.

Figure 3:
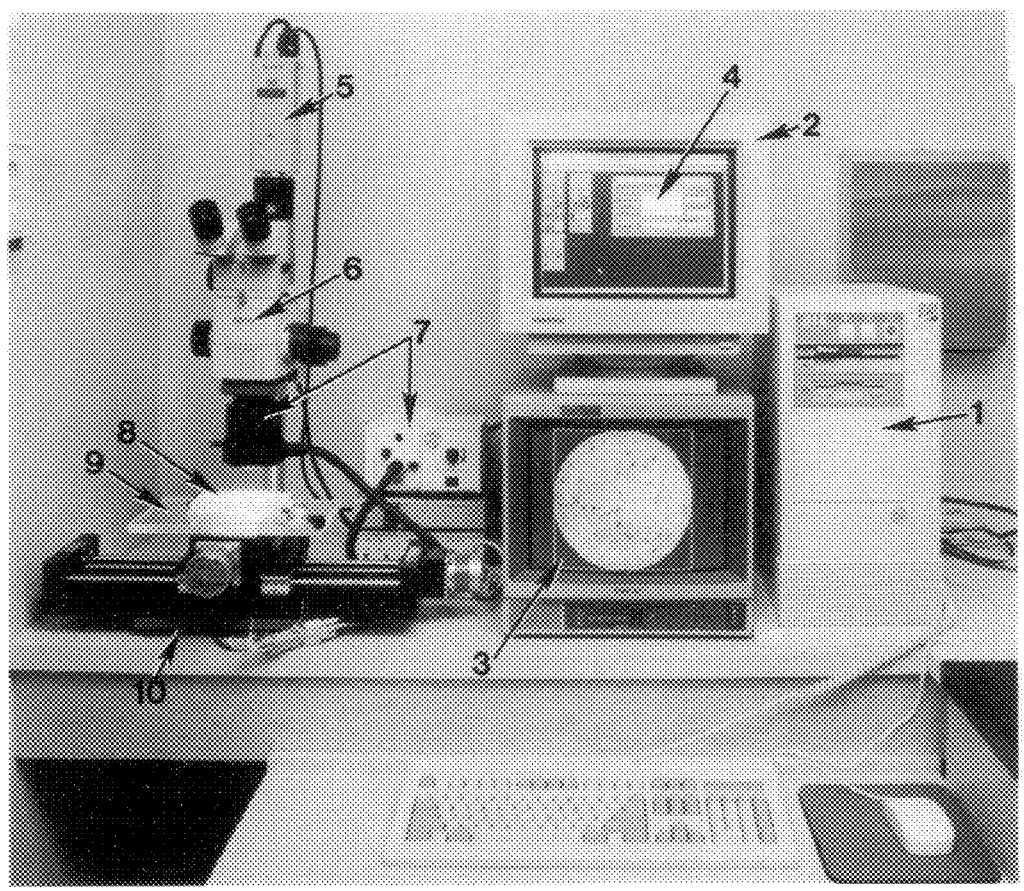
FIG. 3 shows the elements of the quantitative electronic image system of the present invention.
Figure 4:
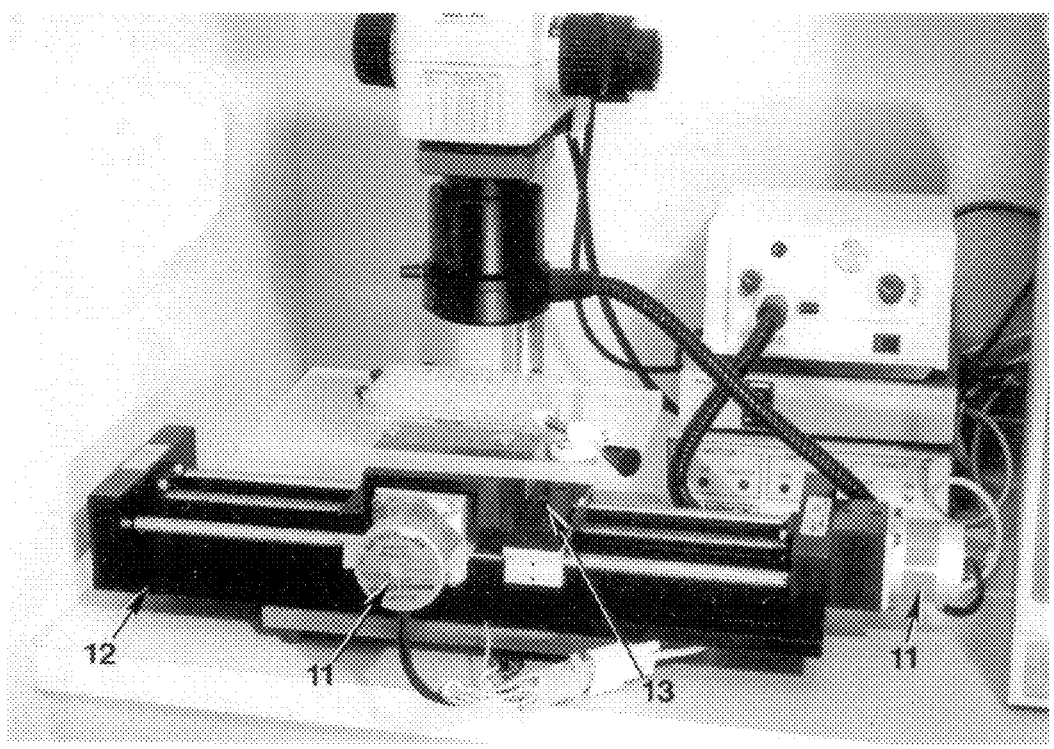
FIG. 4 shows the stage and positioning elements of the quantitative electronic image system of the present invention.

FIG. 4 shows the automated scanning stage (FIG. 3, item 10) in greater detail. This system aligns the test plate (FIG. 3, item 8) on the positioning platform (FIG. 3, item 9) on an X andY stage (FIG. 3, 10) which is constructed of ½ inch polycarbinate plastic with hardened step cap screws. The test plate (FIG. 3, item 8) is pushed against the step screws by a spring plunger, this provides contact to the step screws. The design provides constant positioning repeatability. The stage is mounted directly on a base with a shaft to support the microscope head and CCD camera (5). Stepper motors (11) provide 0.9 degree steps at 400 steps per revolution. For the X axis linear positioning table (12), total travel is 12 inches with an accuracy of 0.0001 of an inch, per one inch travel. For the Y axis linear positioning table (13), the total travel is 4 inches with a similar range of accuracy.

Figure 5:
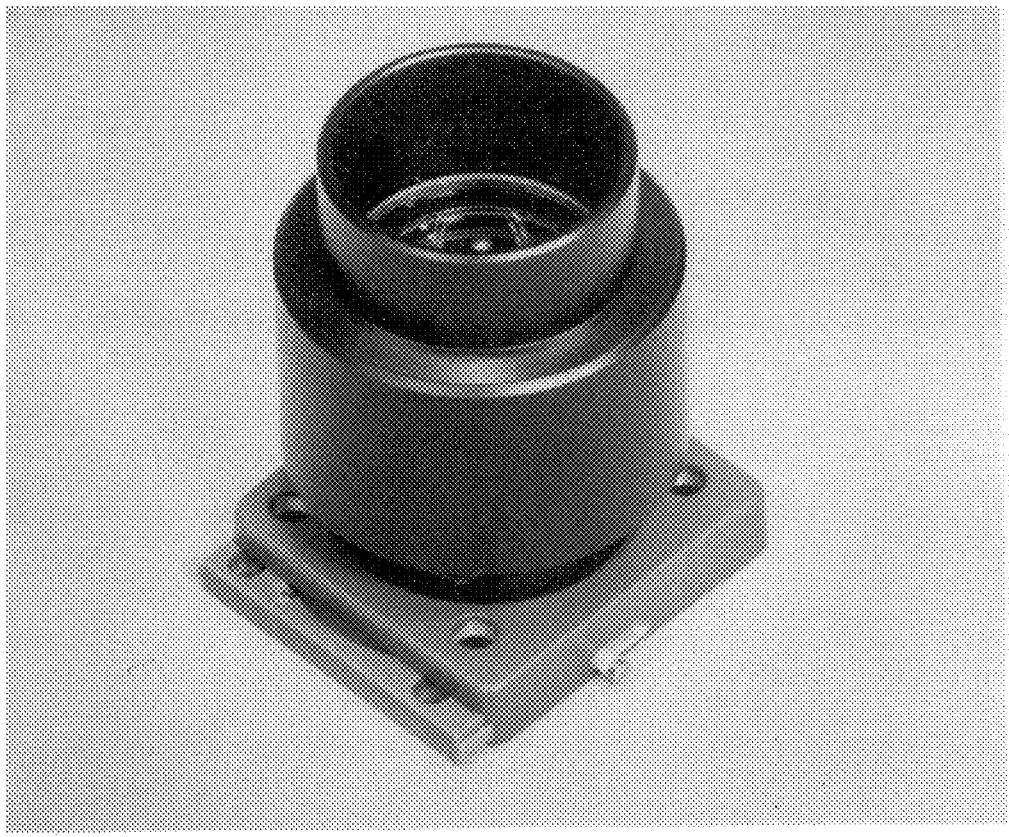
FIG. 5 shows the assembled custom photo tube offset element of the quantitative electronic image system of the present invention.
Figure 6A:
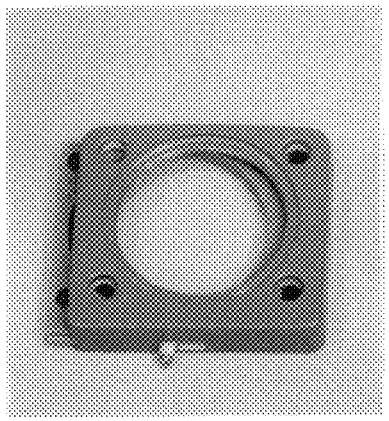
FIG. 6 shows the components of the custom photo tube offset element of the quantitative electronic image system of the present invention.
Figure 6B:
Figure 6C:
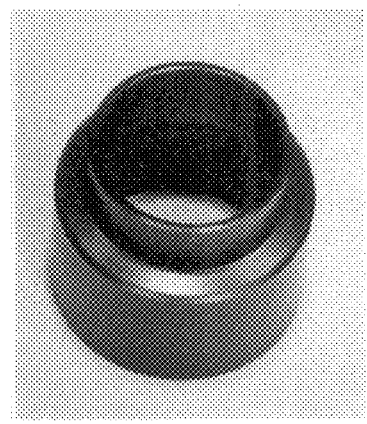

FIGS. 5 and 6 show the custom designed Photo Tube Offset with fiber optic illuminator ring (shown in FIG. 3 as item 7 connected to the Fiber Optic Light Source). This design provides a selection of monocular view or binocular view so that the image is directed entirely to the camera port, eliminating any loss of light. The translator, with stop, is designed by milling two parallel slots on two sides of the existing lens mounting plate. Next a plate is fabricated from Delrin AF plastic with two mating channels that are matched to the milled slots on the lens mounting plate. A positioning stop is milled into the side to give exact alignment. The four mounting holes are duplicated for remounting alignment onto the microscope lens mounting end. The lens is then screwed back into the mounting plate. The ring illuminator adjuster is fabricated from black Delrin plastic, with locking screws. The ring illuminator adjusting unit slides over the lens with the fiber optic illuminator attached. This design (which has been developed for compatibility with the Olympus SZH microscope head) eliminates multiple shadowing of magnified image and optimum light intensity.

EXAMPLE 4

Method of Automated Image Analysis

The conventional ELISA spot approach to detecting and categorizing spots has been visual identification by the human eye. Unfortunately, even with a strong signal, it is difficult for the human observer to reliably locate and categorize numerous spots in an image. As noted in the previous example, the present invention employs a computer coupled to a camera and a microscope to locate and categorize spots in multiple wells of a typical assay plate.

Figure 7:
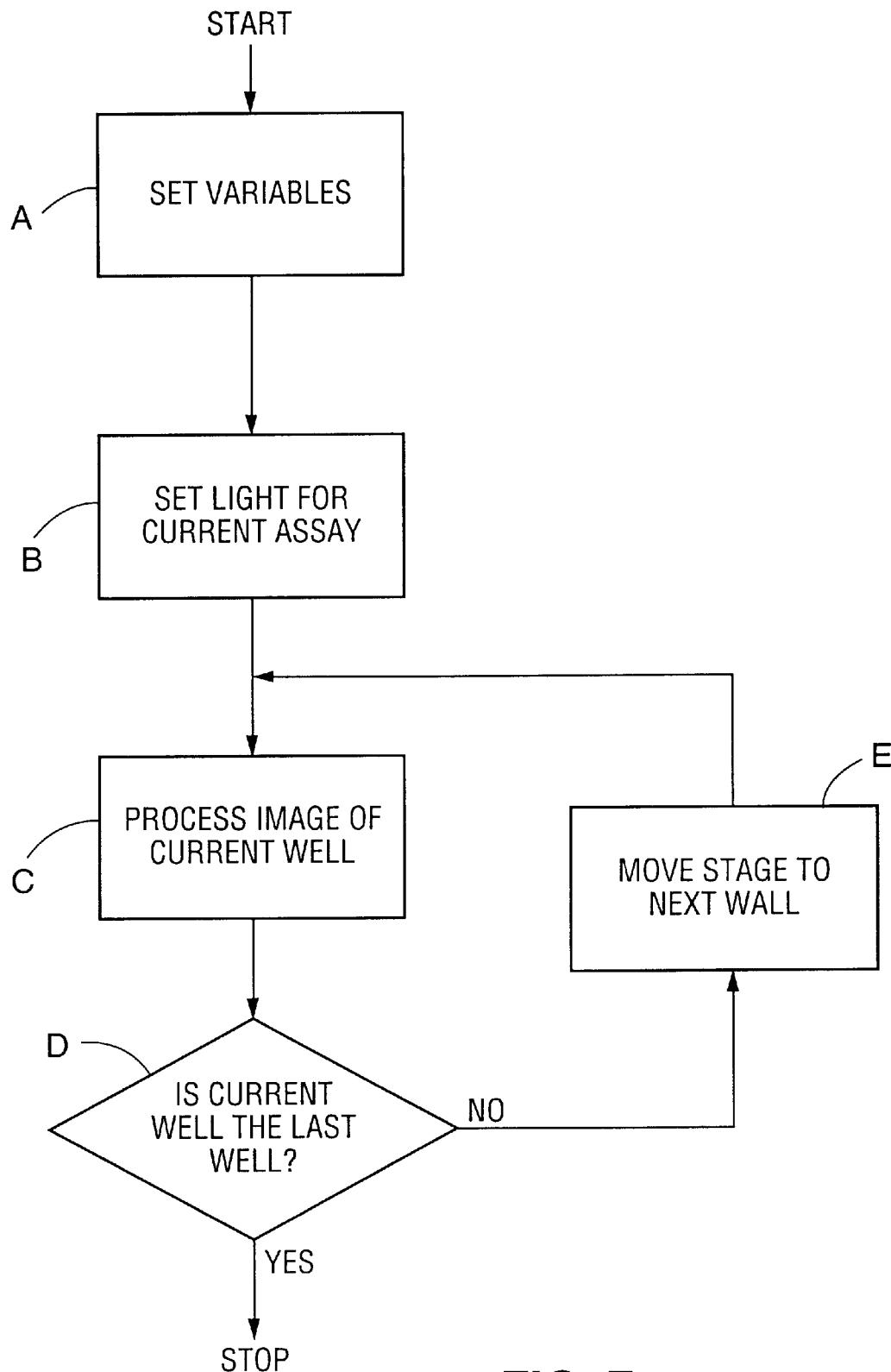
FIG. 7 illustrates a basic flowchart of the processing steps of the automated image analysis method of the present invention.

FIG. 7 illustrates a basic flowchart of the processing steps for the present invention. Specifically, at Step A, a user inputs various variables and configuration data which identify the assay being examined and several examination parameters. These variables include the assay number, the size thresholds and corresponding categories, flags for different save operations, instructions for post assay data analysis, and a standard luminance for the assays.

Step B of FIG. 7 corresponds to procedures for setting the light level for the current assay. This is to provide for a light setting that will provide for optimal luminance match-up for each assay. Luminance match-up is required so that the wells can be examined under the same conditions. A more detailed flowchart of these procedures is described in FIGS. 8A, 8B and 8C.

Step C of FIG. 7 corresponds to procedures for processing the digitized images of each well. Once the computer captures an image of a specific well, specific filtration procedures are executed to clean and clarify the image. Again, a more detailed flowchart of these procedures is described in FIGS. 9A and 9B.

Step D of FIG. 7 is a decisional step wherein the processor must determine if the well currently being processed is the last well. There are many methods for determining this. For example, the user could input the number of wells as an additional variable in Step A. After each well is processed, the processor can decrement this value until the value is zero, at which point, there are no more wells to process. If the current well being processed is the last well, the program ends. If not, step E is executed and the processor moves the stage so that the next well can be viewed by the camera. The program then loops to run steps C and D again until the last well is processed.

Figure 8A:
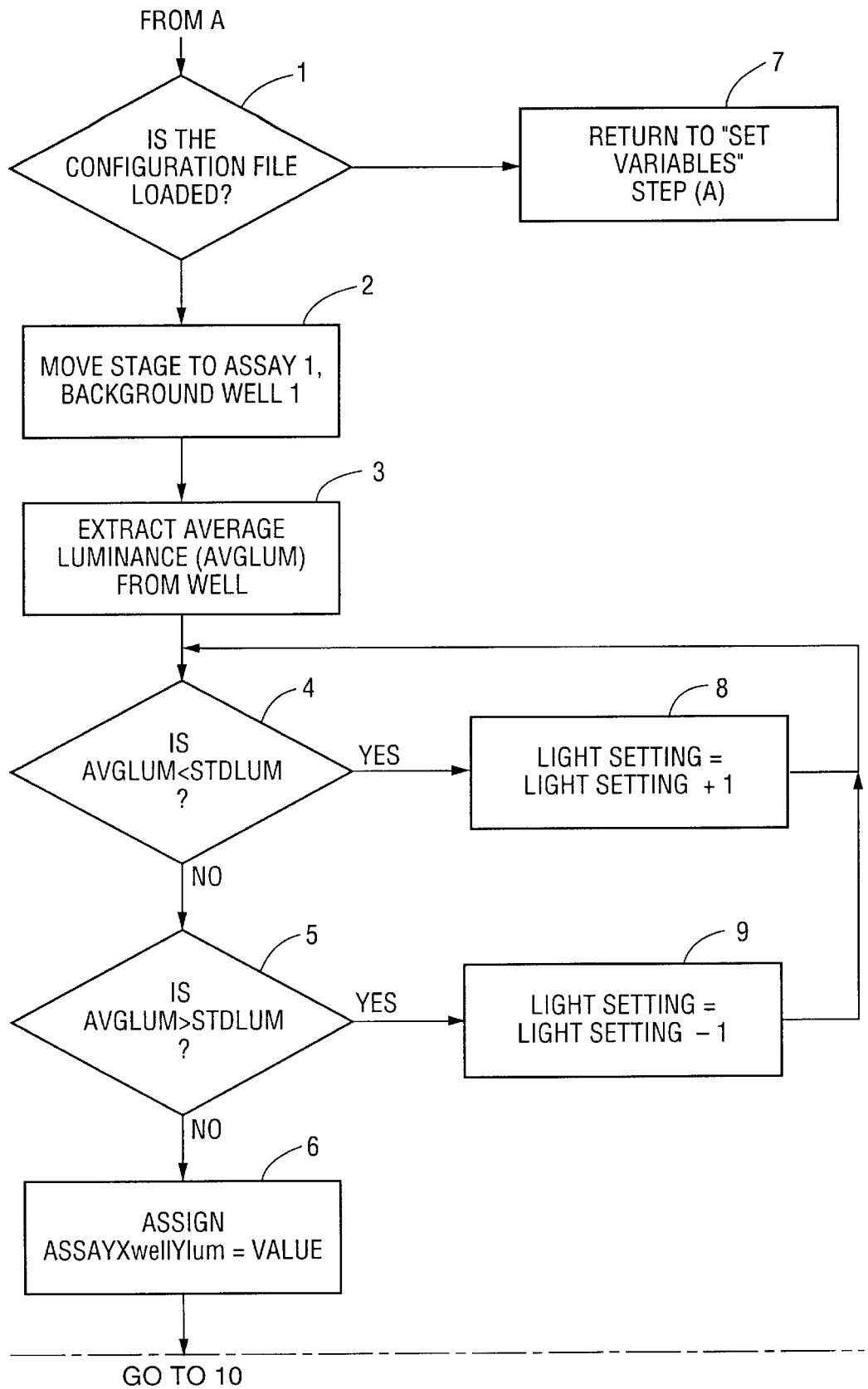
FIGS. 8A, 8B and 8C illustrate the procedure for setting the light level for the automated image analysis method of the present invention.
Figure 8B:
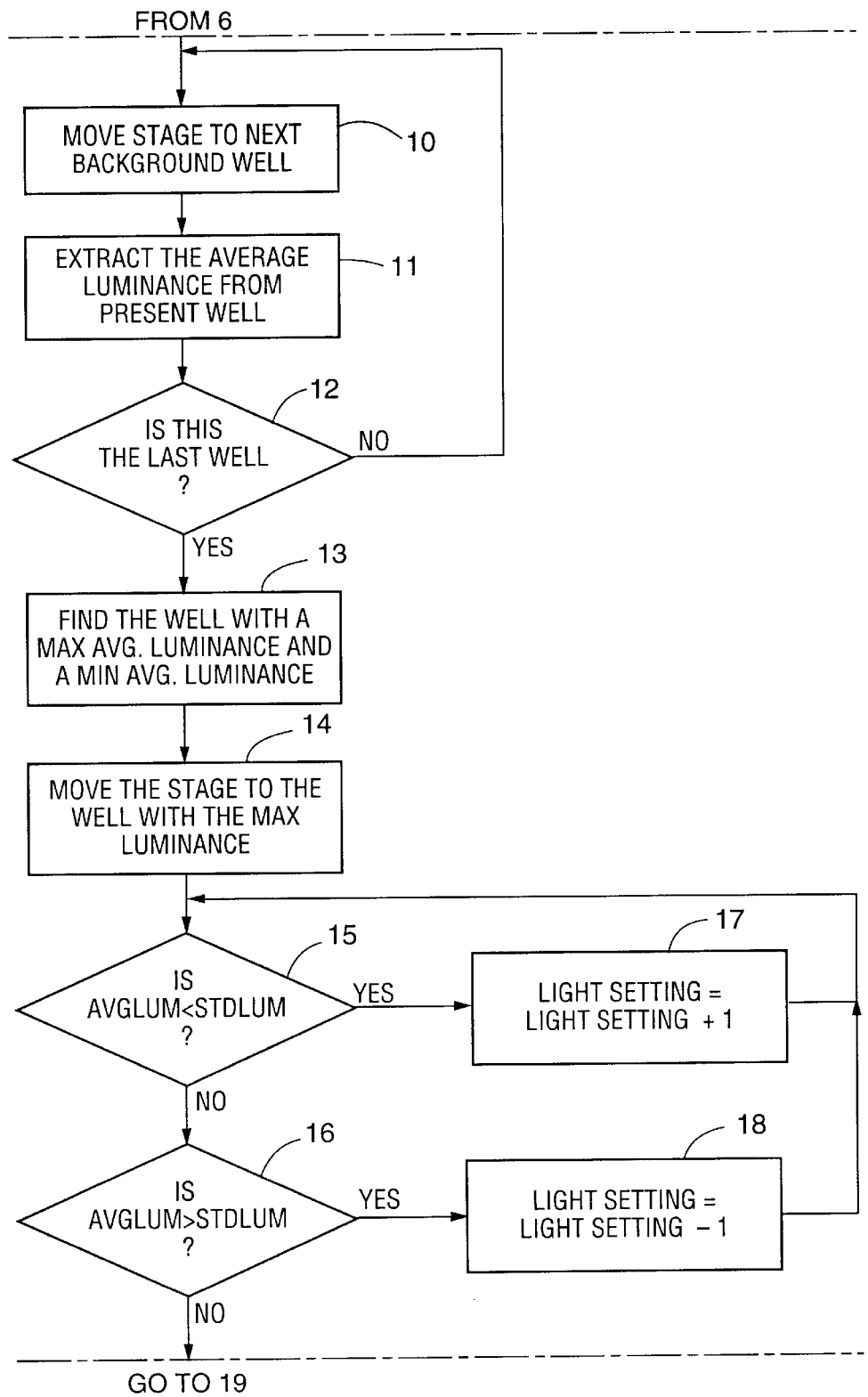
Figure 8C:
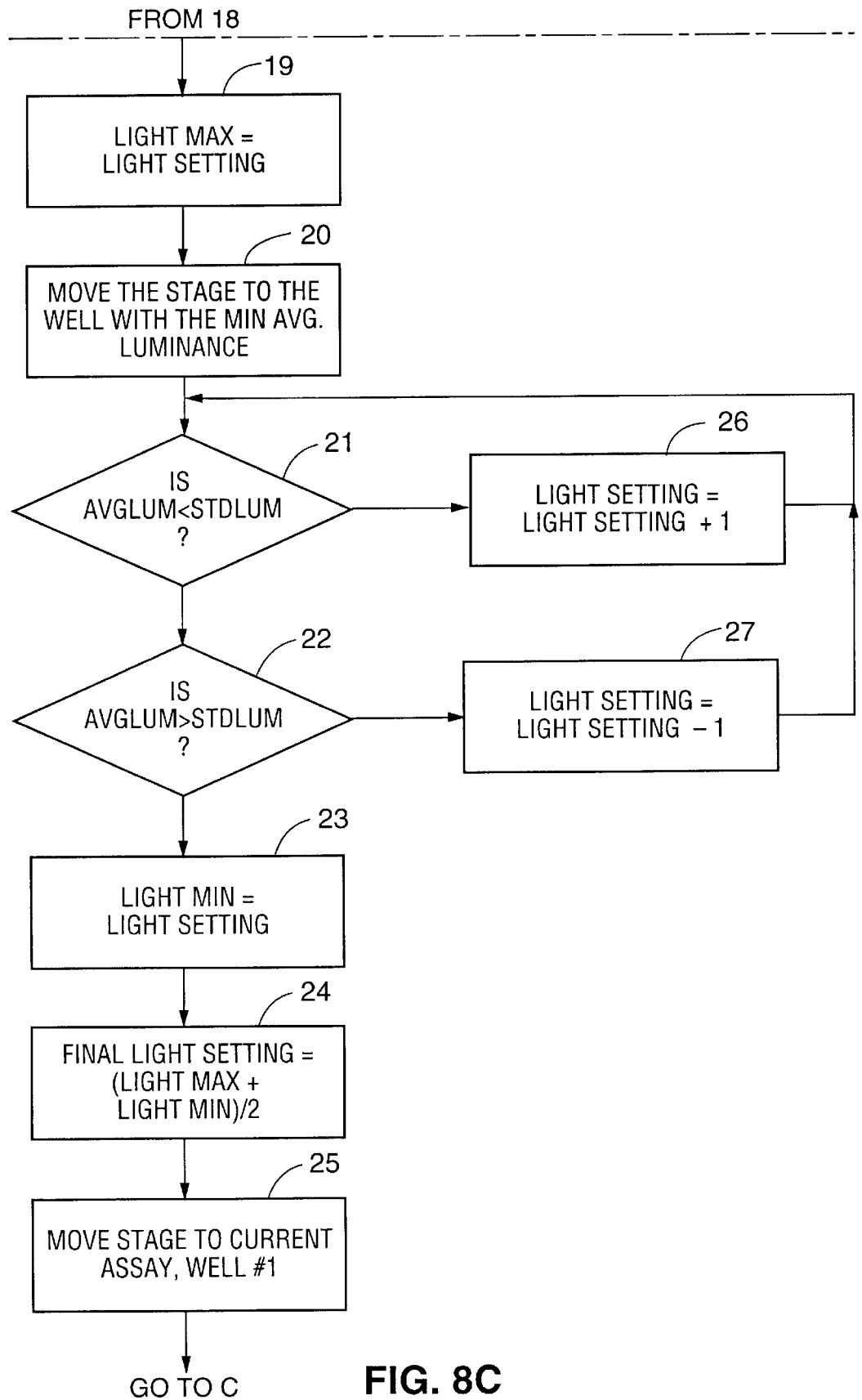

FIGS. 8A, 8B and 8C illustrate the procedure for setting the light level for the current assay. The procedure starts by checking to see if the configuration file and other global variables are loaded (Step 1). If they are not loaded, then the procedure returns back to Step A to have the user input the required variables (Step 7). The stage of the image analysis system is then moved so that background well is visible to the camera (Step 2). The average luminance (avglum) of this well is determined by taking an image of the well and calculating the average red-blue-green luminance values of the pixels in the image. The procedure then runs a loop to adjust the light setting variable. Specifically, the procedure determines, at Step 4, if the average luminance is less that the standard luminance (which should have been input by the user at Step A). If so, the Light Setting is incremented, at Step 8, and the program loops back to Step 4. If not, the procedure determines if the average luminance is greater than the standard luminance. If so, the light setting is decremented, at Step 9, and the program loops back to Step 4. If not, this means that the standard luminance is equal to the background luminance. The average luminance value is then assigned to the variable AssayXwellYlum, where "X" represents the current assay number and the "Y" represents the current well number (Step 6).

The, procedure then continues in FIG. 8B. The stage of the image analysis system is moved so that the next well is visible to the camera (Step 10), and the average luminance is extracted from that well (Step 11). The program then loops (Step 12) until the average luminance values of all the remaining wells are extracted (similarly to the procedure for the first well). Once the average luminance values for the remaining wells are determined, the wells with the maximum and minimum values are located (Step 13). The stage is then moved to the well with the maximum luminance and the average luminance of the well is compared with the standard luminance (Step 15). Steps 15–18 perform the same loop described in Steps 4,5, 8, and 9 above.

The newly determined light setting is then saved as the light max value in Step 19 of FIG. 8C. The stage of the image analysis system then moves to the well with the minimum average luminance value (Step 20). The procedure loops through Steps 21, 22, 26, and 27 similarly to Steps 15–18. The newly determined light Setting is then saved as a light minimum value at Step 23. The final light setting to be used for the current assay is then determined by taking the average of the max and min light settings (Step 24). Now that the final light setting is determined for the entire assay, the stage is moved to the first well in preparation for processing well images to be taken by the camera (Step 25).

Figure 9A:
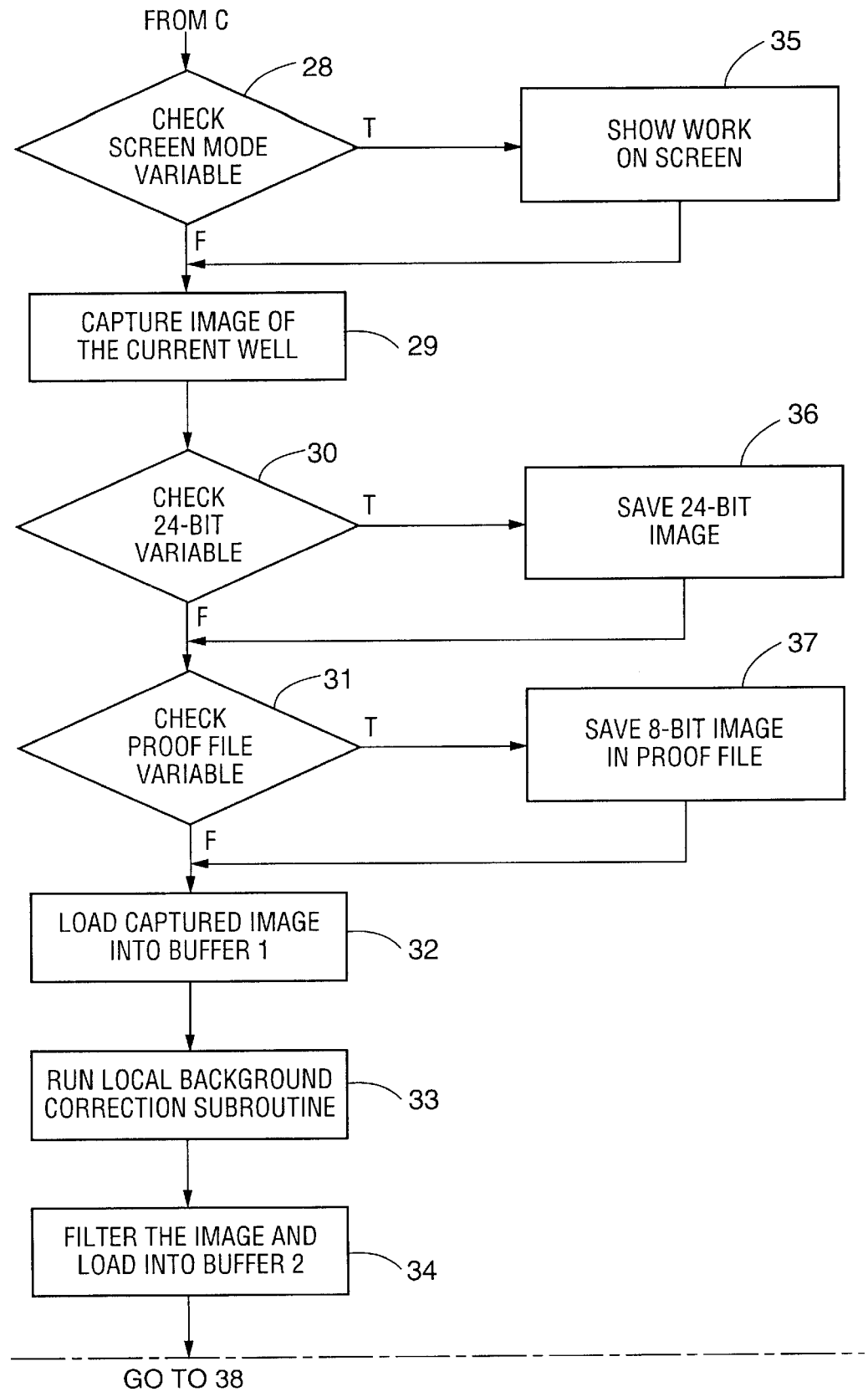
FIGS. 9A and 9B illustrate the steps utilized for processing the well images.
Figure 9B:
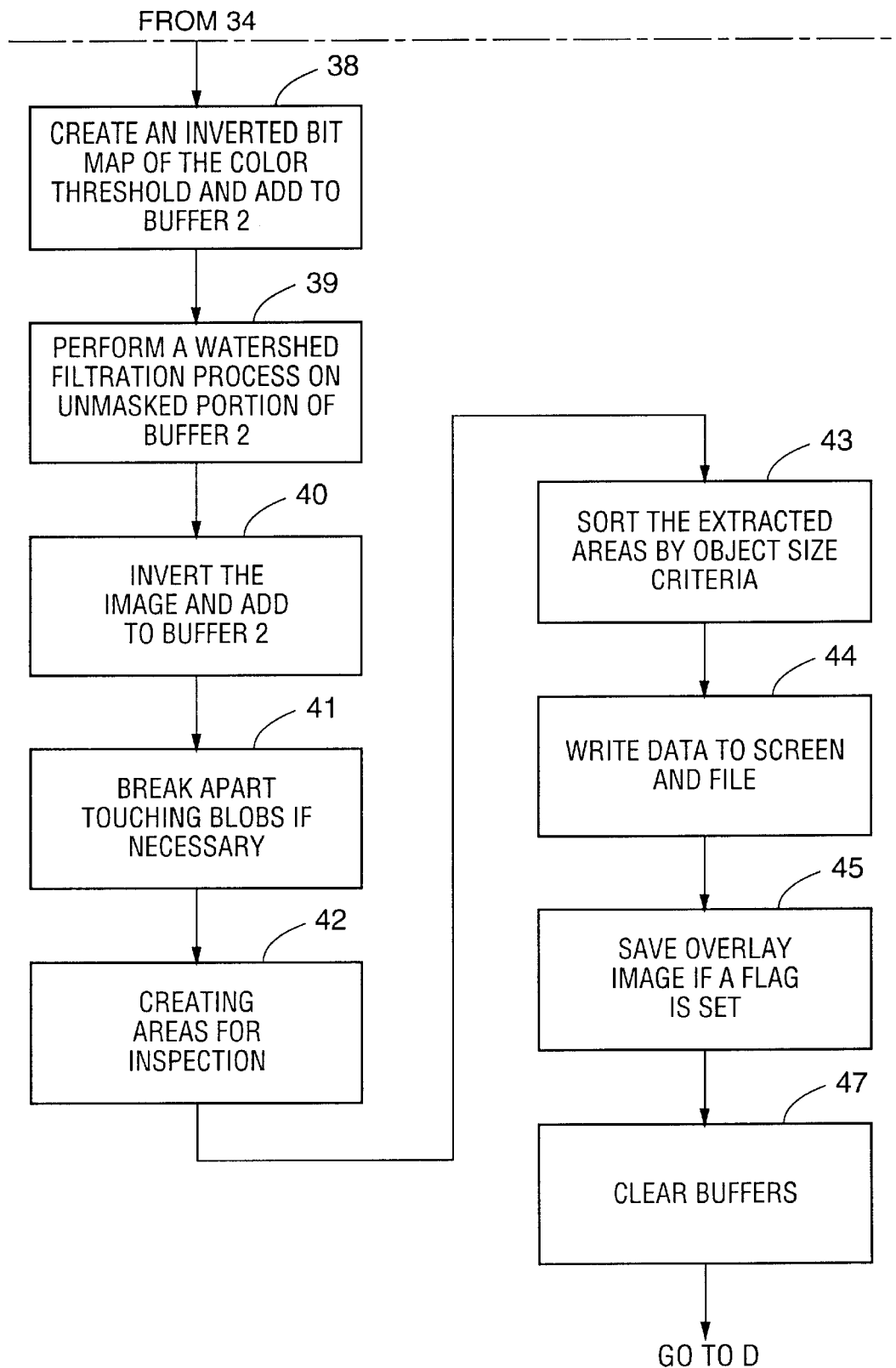

FIGS. 9A and 9B illustrate the steps utilized for processing the well images. The processor first checks the status of a screen mode variable (Step 28). If it is true, the processor will show all intermediate bitmaps (process steps) are shown on the screen (Step 35). This will slow down the processing time but it may be beneficial for users to view intermediate images. The camera then captures an image of the present well (Step 29). Depending on the hardware used, the image signal may be analog, in which case it must be digitized in order for the image to be processed.

The processor then checks two variables, a "24 bit" variable (Step 30) and a "Proof File" variable (Step 31). Depending on whether these variables are configured, a 24 bit image (Step 36) and/or an 8 bit image (Step 37) will be saved, respectively. The 8-bit images in the proof file can be used to create a composite "proof sheet" of all wells collected. The originally captured image is then loaded into Buffer 1 (Step 32).

A local background correction subroutine is executed at Step 33. This subroutine eliminates large scale variations in lighting and coloration caused by uneven lighting and blotchy coloration of the membrane. This subroutine operates by segmenting the image into a grid according to x, y dimensions chosen by the user. (The default is 64:64 pixels) A luminance array is created by extracting the average luminance from each segment and placing the value in the corresponding array position. The two dimensional array is then fit to a polynomial curved surface to provide a smooth transition from point to point on the array. A luminance grid is constructed to fill in all the points in the original image size and then applied to the image. This process is performed for each of the image planes (Red, Green, Blue) separately, to correct the luminance for the entire image. By keeping the pixel grid sufficiently large and the polynomial order sufficiently small, features of the size of ELISA Spots remain intact, while the background is made uniform.

After the background has been smoothed, the image is filtered and loaded into Buffer 2 (Step 34). The filters used here are convolve filters, which can be configured for many different purposes. A convolve filter alters each pixel in an image according to its own luminance and the luminances of its neighboring pixels. Filters can be of various sizes, depending on how far from the target pixel the user wants to examine other pixels. For example, a first 3×3 filter of equal weight is applied followed by a second 5×5 filter which is configured to amplify transitions from light to dark. The first filter is a standard 3×3 averaging filter that smooths out fine variations in the image in preparation for the second filter. The second filter enhances regions that are dark in the center, surrounded by relatively light regions, i.e. ELISA spots. The second filter is also unevenly biased in that it lightens the overall image while drastically darkening the spots. (In-between the extremes, the contrast between levels of luminance are increased.) Therefore, the luminance contrast and detail are enhanced while at the same time, lowering the background level.

Once the background has been smoothed, an inverted bitmap is created based on the color threshold obtained from assay parameters entered by a user in the beginning of the program. This inverted bitmap is superimposed on the image in Buffer 2 as a mask (Step 38). An inverted bitmap is one where the intensity levels of the pixels are inverted so that, white pixels become black pixels and vice-versa. In otherwords, a white mask based on an inverse of the bitmap of the threshold is created and superimposed on the image from Step 37 which resides in Buffer 2. The effect is to eliminate those pixels not meeting the threshold. The threshold is a predetermined pixel intensity level which is set by the user. Thresholds are utilized so that only those objects of sufficient intensity levels will remain for later analysis. The remaining bits that pass the threshold are saved to Buffer 2.

A watershed filtration process is then performed at Step 39. This is a widely published and commonly used filtration process known in the art. Its function is to separate objects in an image on the basis of variations in luminance between the two. Unlike blob separation routines that are threshold based, this routine can distinguish objects of widely differing luminances. In other words, it can identify spots even if some are light and others are dark, so long as there are relatively lighter areas between them.

The watershed filtration process used in the present invention basically works as follows. A bitmap is created for each threshold from 0–255 (black to white). This means that a virtual image is created which is all black where the source image is below threshold (darker than the threshold luminance value), and all white where it is equal to or higher than the threshold. These bitmaps are examined in sequence, from the threshold where all bits are black until all bits are white. For each level, the black space, between white areas are skeletalized (reduced to a single line along the longest axis). This skeletal image is retained and added to as each bitmap is examined in turn. As new white areas emerge, they generate new dividing lines. The result is a map of black dividing lines on a white background.

After the watershed filtration process is performed, the image is inverted and added to Buffer 2 (Step 40). To perform the add process between Buffer 2 and the watershed bitmap, the bitmap must be black with white lines. This is accomplished by inverting the bitmapped image; in essence, making a negative image. By performing the add process, the luminances values of the corresponding pixels in the two images are added together. The effect is that those areas in the image that are important remain, and those that are not, are whited out.

Before the final image can be examined and the ELISA spots identified and categorized, one last procedure may need to be performed. This involves breaking apart blobs (which are masses of overlapping spots). As explained above, the watershed filter separates regions on the basis of luminance variations. In densely populated wells, there can be spots that overlap such that the connecting area is of a constant luminance or saturation. These spots will not be separated by the watershed filter. For these, a separation must be done based on binary morphology (black and white shapes).

Binary morphology involves extracting a single black and white bitmap from the image according to a set threshold. A series of erodes are then performed. (An erode is a process wherein the edge pixels are removed from the edges of all objects, making them smaller.) When only one pixel is left for each object, the process stops. Any region that has a constriction in it (a dumbbell shape) will erode to two points. Next, the same number of dilates is performed, adding one pixel to the perimeter, however, areas are not allowed to overlap, thus maintaining separation of objects.

The final image of the well can now be processed in Step 43 wherein Spots are identified and categorized based on user input threshold values. There are many well known methods for locating and measuring objects in a digitized image. Once all of the objects are identified and categorized, the data is written to the monitor, and to a save file (Step 44). A user can then control a saving operation of the overlay image at Step 45 and clear the buffers at Step 46 in preparation for another well.

The flow logic then continues back to Step D from FIG. 7 wherein the computer determines if there are any remaining wells and reruns the processing subroutine if necessary.

EXAMPLE 5

Peptide Screening

In this example, the microwells of the present invention are employed to screen and identify the determinants (i.e. MHC-bound peptides of the antigen generated by intracellular processing) that T cells recognize, using peptides. Usually, in studies that involved peptides, a few randomly chosen sequences of the antigen were tested as peptides. However, even overlapping sequences that walk down the molecule in steps of 5 to 10 amino acids do not necessarily detect all determinants. By contrast, in this example overlapping sets of peptides were employed that walk the molecule amino acid by amino acid. This peptide scan includes every possible determinant on an antigen and provides an exact mapping of the T cell repertoire.

While this assay system has been employed to test for antigen specific CD4 cells [G. Gammon et al., "T Cell Determinant Structure: Cores and Determinnant Envelopes in Three Mouse Major Histocompatibility Complex Haplotypes" J. Exp. Med. 173: 609–617 (1991)], the present invention allows for testing of CD8 cells. CD8 determinant mapping for HIV identifies possible peptides for vaccines. Determinant mapping for autoantigens in autoimmune disease has prognostic and possible therapeutic consequences.

For determinant mapping, Myelin Basic Protein ("MBP") peptides that walk the MBP molecule amino acids by amino acid were used. These peptides produce clear data in SHIV-ERER mice. The peptides can be frozen without loosing bioactivity at 14 $\mu$M concentration in HL-1 medium, which is 2× the optimal concentration for the bioassay. Thus, the large number of peptides involved do not have to be diluted and plated for each experiment, but can be freshly thawed from storage. The entire peptide series was diluted, pipetted and frozen series in advance and, on the day of experiment, the required number of plates were thawed.

The number of cells available from patients can be limiting; one million cells can be obtained from one milliliter of blood and usually fifty milliliters of blood is available per patient (i.e. fifty million cells may be the total cells available for the assay). Because $2 \times 10^5$ cells per well provides clear results with the plate of the present invention, this is sufficient for testing 250 peptides, which constitutes an average size protein. However, by miniturizing the plates (e.g. to 50 microliter wells), one can test for 1000 peptides, which can cover even the larger proteins. The entire peptide series can be tested on an individual. The plating of the cells can be performed with 12 channel pipetors into the freshly thawed plates, reducing the time involvement on the first day of the assay to a couple of hours.

In this example, PBL cells were plated at $2 \times 10^5$ cells per well into 96 well microtiter plates containing the hydrophobic membrane precoated with capture antibody. The cells were incubated in the wells with antigen for 24 h at 37° C., 8% $CO_2$. During this culture period, T cells with specificity for a given peptide will be activated and start secreting cytokines and other cellular products, which will be captured by the appropriate antibody on the plate around producing cells. Thus, secreting cells (antigen specific memory cells) are surrounded by a "spot" of the cytokine.

Figure 10:
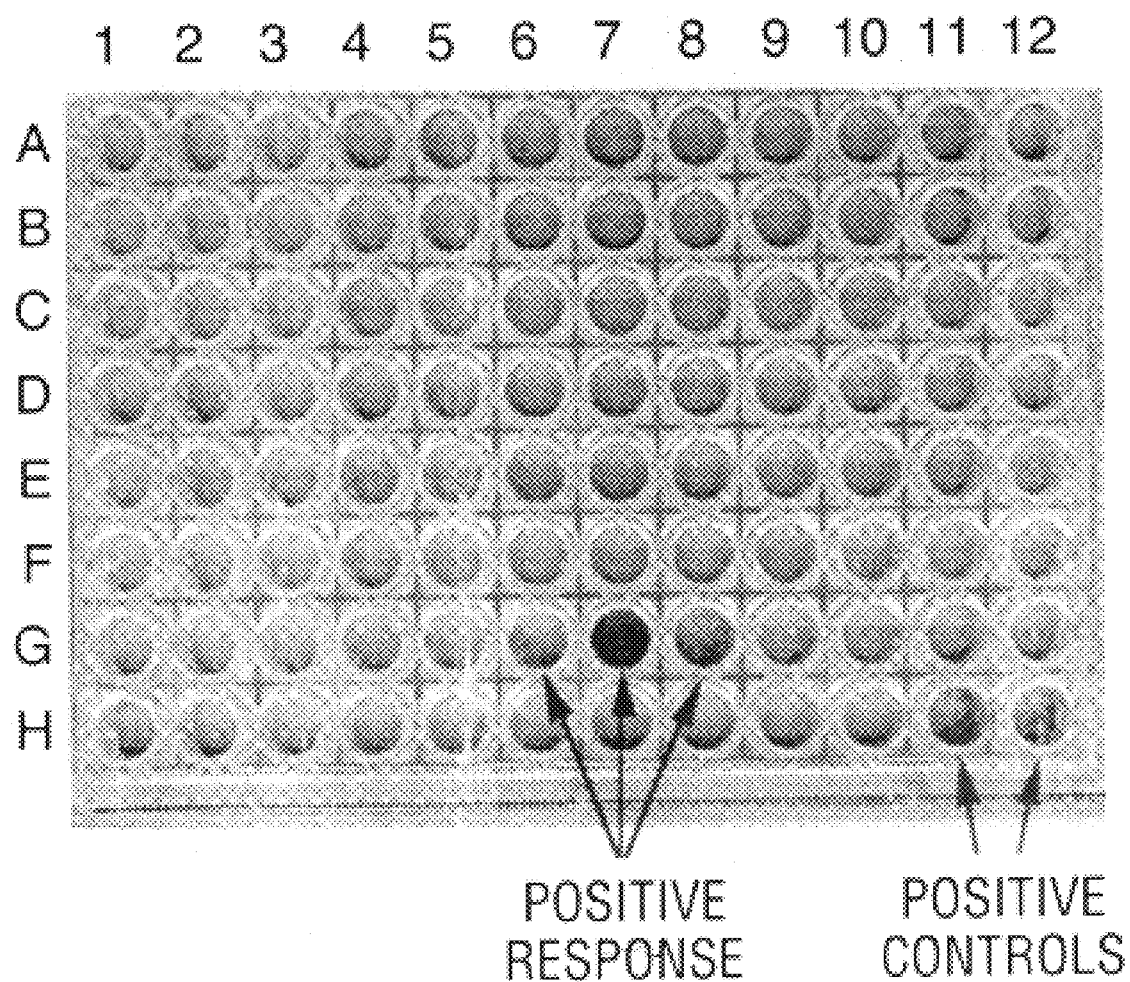
FIG. 10 is a photograph of the results of peptide screening using the microplates of the present invention.
Figure 11A:
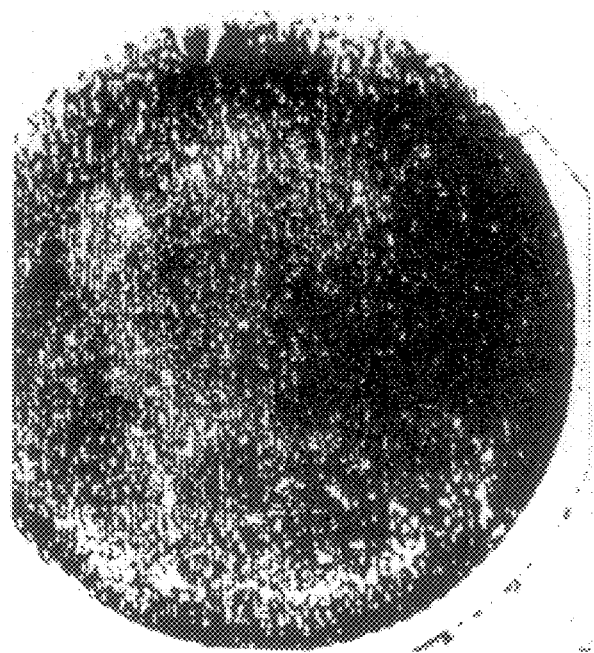
FIG. 11A–11G are photographs showing the two color assay of the present invention.
Figure 11B:
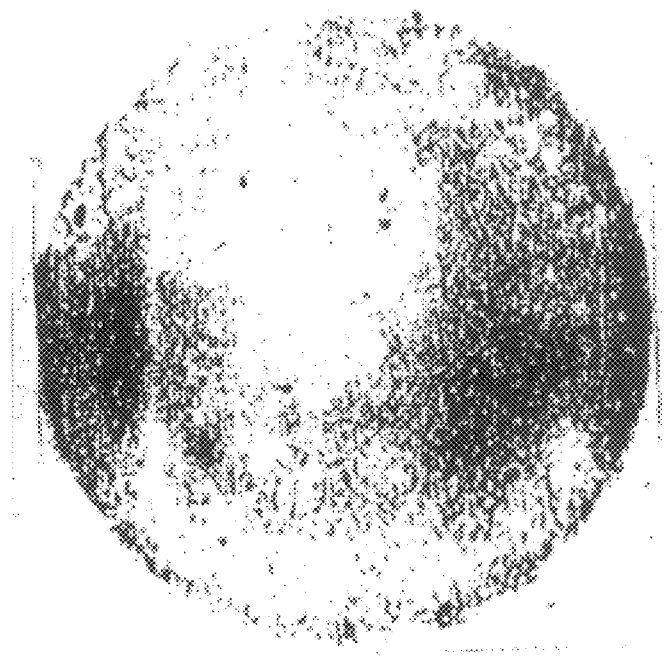
Figure 11C:
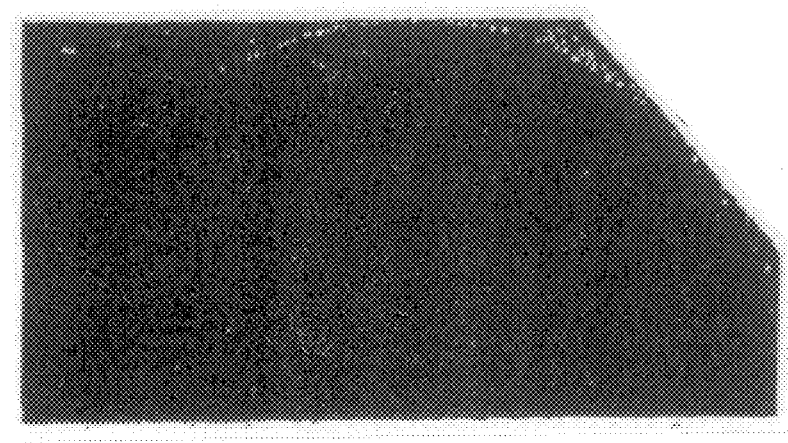
Figure 11D:
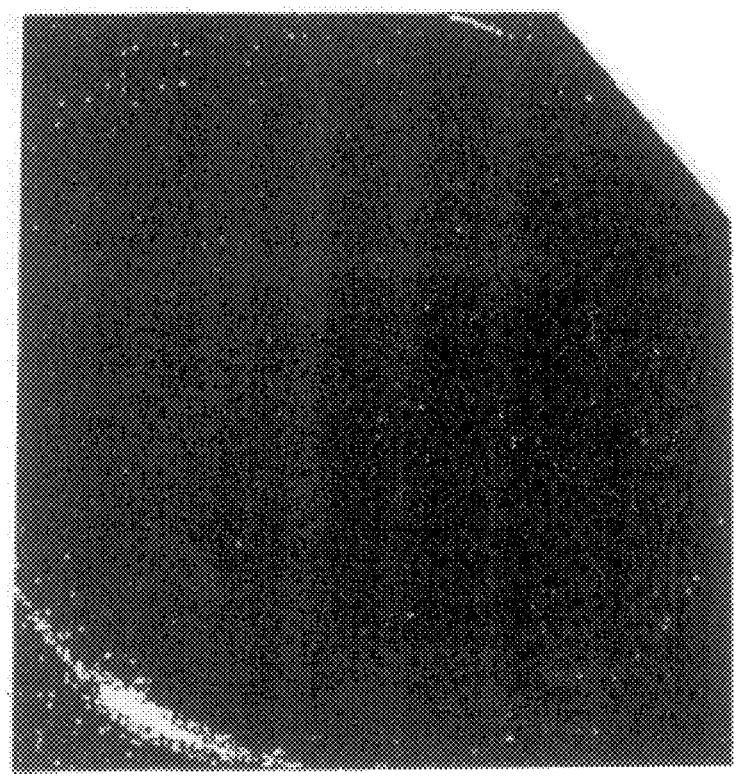
Figure 11E:
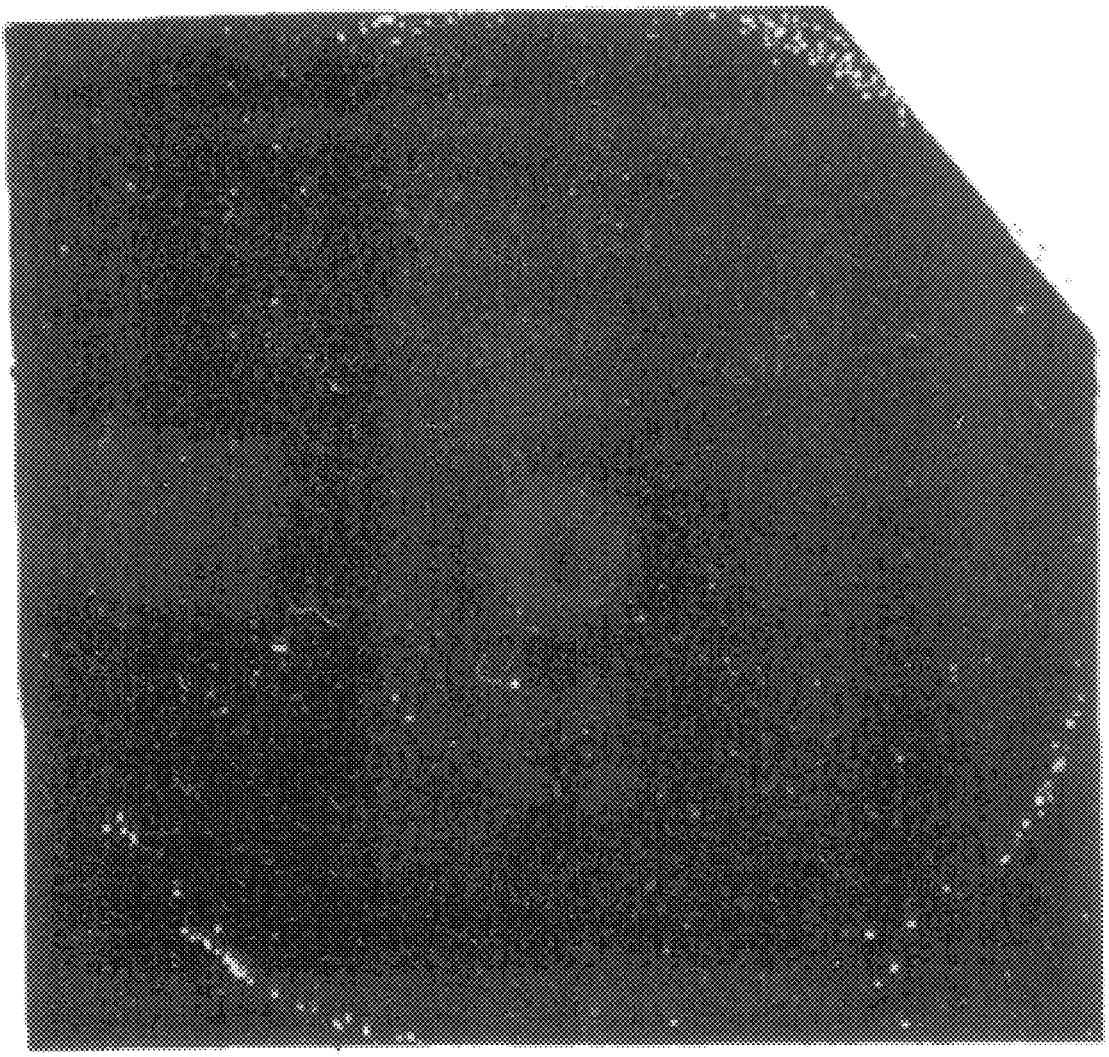
Figure 11F:
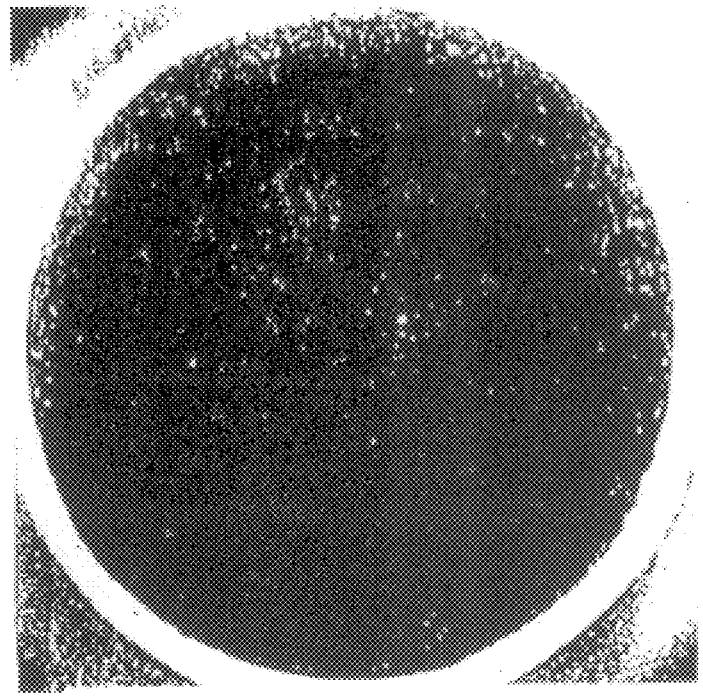
Figure 11G:
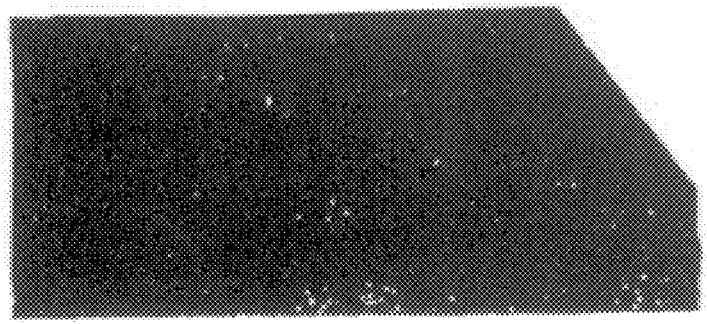

After an additional culture (24 hours), the cells are then washed away and the bound cytokine is detected by a biotinylated second antibody that is specific for the same cytokine but recognizes a different determinant on it. The plate bound second antibody will be visualized with the tetrazolium-bromochloroindolyl phosphate reaction or other enzymatic reactions. The "spots" are stable for about a year (see FIG. 10).

The numbers of spots in antigen containing wells vs. wells containing medium alone or irrelevant antigens establish the number of antigen specific cells in the culture. Since $2 \times 10^5$ cells were plated to each well, the absolute frequency represents the frequency of antigen reactive T cells in $2 \times 10^5$ T cells of the given specificity within the cell pool tested.

EXAMPLE 6

Two Color ELISA Spot Assay

In this example, the membrane is prepared as in Example 1, except that a second capture reagent is used as well. To prepare the membrane for a two color assay, two (2) capture reagents (anti-IFN$\gamma$ and anti-IL5 antibody) are used simultaneously (for additional capabilities, still additional capture reagents can be employed for a "multicolor" assay).

Cells are again plated (~$5 \times 10^5$ cells) and only the antigen specific T cells will be stimulated by the antigen to release secretory products. However, in this case, the membrane is capable of detecting both IFN$\gamma$ and IL-5. After the culture period and washing described in Example 1, a second detection reagent is employed together with the first detection reagent. In this case, ALPH labelled anti-IL-5 detection antibody is added (alternatively, fluorochromes emitting different colors when excited by UV light permit two or multicolor assays e.g., FITC:green, PE:red). As substrate, 5-Bromo-4-chloro-indolyl-phosphate ("BCIP") is used with NBT (BCIP is available commercially from Pierce); ALPH cleaved NBT/BCIP gives a blue product. In the two (2) color assay, spots originating from cells that secreted one of the products only, will appear in single color (e.g., red or blue), while cells secreting both will have the color overlay, appearing as violet. The extent of color overlay in the two (2) color assay permits quantification of the relative quantity of each component released by the double producing cell (i.e. a more red-violet spot means a cell that produces both IFN$\gamma$ and IL-5, but IFN$\gamma$ dominates over IL-5 production). The exact qualification requires image analysis, as described above.

A Th1 and a Th2 clone were tested. One clone, 4R9, derived from a B10.A(4R) mouse, is CD4$^+$ and allo-specific for I-A$^k$. When stimulated with anti-CD3 antibody in the presence of SCID feeder cells, this clone secretes IFN$\gamma$, but no IL-5, as measured by ELISA in the culture supernatant (not shown). Thus 4R9 is a Th1 clone. The other clone tested, M33, was derived from an SJL mouse, is CD4$^+$, I-A$^u$ restricted and specific for a kidney autoantigen, RTA. When CD3 stimulated, M33 produces abundant IL-5, but no IFN$\gamma$, as judged by ELISA (not shown). Thus, M33 is a Th2 clone.

In this assay the clones were tested with SCID APC in the presence of anti-CD3 antibody. The reason for using this experimental setup is two-fold. First, since the 2 clones utilize different restriction elements for cognate antigen recognition, it is necessary to use an experimental condition in which both clones can be stimulated by a single type of APC and stimulus. Second, since there are no T cells in SCID mice, there is no alloresponse by the feeder cells to the clone and the CD3 antibody will not cause stimulation in the feeder cells population, either. Furthermore, unirradiated SCID spleen cells were used as APC, this setup also allows for the determination as to whether non-lymphocyte lineages will produce the cytokines in question in a bystander fashion, e.g., it is conceivable NK cells secrete IFNγ in response to the IL-2 released by the Th1 clone (in which case, the frequency of spots should be higher than the number of cloned cells plated per well).

All the ELISA spot wells shown in FIG. 11 contain 2×10$^5$ unirradiated SCID spleen cells and anti-CD3 antibody (2C11) at 5 μg/ml. Additionally, each well contained cloned T cells as indicated. A single color IFNγ assay was performed in A, B and C (HARP-XMG1.2 antibody with AEC substrate that gives a red product) and a single color IL-5 assay was performed with D, E, and G (ALPH-TRFK4 antibody with NBT/BCIP substrate that gives a blue product). In F, a 2 color assay, simultaneously measuring both IFNγ and IL-5 is shown.

The results show that, when stimulated, clone 4R9 produces IFNγ (FIG. 11 A & B), but no IL-5 (G), i.e., 4R9 is a Th1 clone, while clone M33 produces IL-5 (D & E), but no IFNγ (C), i.e., M33 is a Th2 clone (unstimulated clones did not produce cytokines, not shown). Second, the number of spots detected correlates well with the number of activated T cells present in the wells, e.g., in A, and D 103 and 188 spots were counted by image analysis from the ~200 cells plated; in B and E, 39 and 45 spots were detected from the ~50 cells plated. Therefore, the ELISA spot assay detects individual cells, directly measuring frequencies. Importantly, the number of spots detected did not exceed the number of cells seeded per well which shows that there was no bystander reaction.

From the results in F of FIG. 11, it is clear that simultaneous measurement of two cytokines is feasible at the single cell level using a two color ELISA spot assay. (Note: in the figure, there are no violet spots, since there are no cells producing both cytokines; but where freshly isolated cells are used, violet spots are seen, suggesting a Th0 phenotype.)

EXAMPLE 7

Mixed Lymphocyte Culture

In this example, the ELISA spot assay of the present invention is used as a functional measurement of alloimmune responses. Alloresponses were measured in naive responder mouse splenocytes upon stimulation with irradiated allogeneic stimulator splenocytes. A Balb/c (H-2$^d$) anti-SJL (H-2$^s$) mixed lymphocyte response (MLR) was set up by mixing 8×10$^5$ responder splenocytes (H-2$^d$) with 4×10$^5$ irradiated stimulator splenocytes (H-2$^s$) in 200λ of HL-1 media (serum free), in 96 well ELISA spot plates that were precoated with antibodies to IL-2, IL-5 or IFNγ. A strong proliferative response is detected and the secretion of Th1 (IFNγ)—but not Th2 (IL-5) cytokines—was measured in culture supernatants. In addition, there was CTL killing of SJL target cells (Table 2).

TABLE 2

| MLR | Proliferation (cpm) | IFNγ (u/ml) (Th1) | IL-5 (u/ml) | % cytotoxity (80:1 E:T ratio) |
| --- | --- | --- | --- | --- |
| H-2d anti H-2d | 15467 ± 4328 | 14 | 0 | 9.6% |
| H-2d anti H-2s | 109986 ± 12921 | 50 | 0.1 | 71.1% |

The ELISA spot assay was evaluated visually (not shown). The Balb/c (H-2$^d$) anti-SJL (H-2$^s$) response was primarily of a Th1 phenotype, with strong IL-2 and IFNγ, but essentially no IL-5 production. Control wells with stimulators alone, responders alone, and H-2$^d$ stimulators mixed with syngeneic, irradiated H-2$^d$ responders all revealed no spots for any cytokine (not shown). Similar assays were performed in multiple strain combinations with equivalent results (not shown), showing that the quality of the response is not strain specific.

Quantitative analysis (spots per 10$^6$ splenocytes) for each cytokine reveals 180–250 spots per million responder splenocytes plated for both IFNγ and IL-2, while<5 per million IL-5 spots are detected. These numbers are representative of four (4) different experiments studying the Balb/c anti SJL alloresponse. Notably, these responses are 5–10 greater than the antigen-specific responses (which are typically 15–30 spots per million cells) from the same mouse strain.

In order to verify that the assay is quantitatively reliable, a similar ELISA spot analysis was performed on serially diluted samples, and found that the number of responding cells falls linearly in relation to the serial dilution. Thus, the ELISA spot assay yields reproducible quantitative and qualitative information regarding the alloimmune response.

EXAMPLE 8

Human Transplant Recipients

Given the ability of the assay of the present invention to detect antigen-specific responses (see above), the assay is also clearly suitable for the study of human alloresponses in the transplant setting, including but not limited to the testing of immunosuppressed transplant recipients. The present invention contemplates the use of the ELISA spot assay as a) a functional predictor of allograft survival in cadaver and living related renal transplant recipients, and b) a tool for monitoring the level of immunosuppression in renal allograft recipients.

96 well ELISA spot plates are coated with capture antibody for either IL-2, IL-4, IL-5, IL-10, or IFN in PBS. Peripheral blood lymphocytes (PBLs) are prepared from normal human volunteers, mixed in various stimulator/responder ratios in 2 mls of complete RPMI in a 24 well plate. After a 12–72 hour activation (IL-2 and IFN can best be detected at 12–24 hours, while IL-4, IL-5, and IL-1 require 36–72 hours, and more preferrably 48 hours), the cultures are harvested, washed, and added to the precoated ELISA spot plates. After another 24 hours the cells are washed from the plates and second detection (biotinylated or directly horse radish peroxidase (HRP) conjugated) antibodies are added to the wells. The plates are washed after an overnight incubation, and a tertiary reagent (streptavidin-HRP, Dako, Denmark) is added, if needed. After a final wash, the chromogen reagent (AEC, Sigma, St. Louis Mo.) is added, and the resulting allospecific cytokine spots are analyzed by the image analysis computer program as described above.

While it is not intended that the assays of the present invention be limited by the use of particular antibodies, work with human PBLs has resulted in the determination that the antibody combinations set forth in Table 3 can effectively detect human cytokines in recall responses to common antigens.

TABLE 3

| Cytokine | Coating antibody | Detection antibody |
|---|---|---|
| IL-2 | BG-5 (Serotec) | Rabbit polyclonal (BD) |
| IL-4 | 8D4-8 (PHRM) | MP4-25D2 (PHRM) |
| IL-5 | JES1-39D10 (PHRM) | JES1-5A10 (PHRM) |
| IL-10 | JES3-9D7 (PHRM) | JES3-12G8 (PHRM) |
| IFN | MA700 (ENDO) | MA701 (ENDO) |

Blood samples will be obtained from normal human volunteers in heparinized green top tubes, and rocked gently at room temperature until ready for use. PBLs will be prepared by standard Ficoll Hypaque centrifugation and counted. By these methods, one can obtain between $1 \times 10^6$ and $3 \times 10^6$ PBLs from each milliliter of blood. All experiments will be performed using complete RPMI media.

In some instances, T cell enrichment is perfered. T cells will be enriched from PBLs using human T cell isolation columns (R and D Systems), as per manufacturer's recommendations. In other instances, depletion of T cell subtypes is desired. Depletion of T cell subtypes will be performed by standard methods, using OKT3 (anti-CD3), OKT4 (anti-CD4), or OKT8 (anti-CD8), and rabbit complement (Cedarlane, Hornsby Ont). Aliquots of the resultant cells will be washed and stained with FITC conjugated antibodies for phenotyping by FACS. The antibodies are isolated from hydriboma supernatants grown in our laboratory by standard methods.

The alloimmune responses in normal individuals will produce primarily Th1 type cytokines, i.e. IL-2 and IFN, with little IL-4, IL-5 or IL-10. It is expected that detected alloreactive responder frequencies in normal individuals will fall in the range of 0.1–10% of the responding T cells. The results for immunosuppressed individuals may vary, but it is expected that the cytokine production will decrease in strength and the clonal size of the response will also be relatively decreased. With sufficient numbers of normal individuals for comparison, an immunosuppressed individual who shows very little relative decrease in response may show signs of allograft rejection.

While it is not intended that the present invention be limited by the precise condition of the patients, recipients of living related donor renal allografts, and their donors are preferred. Patients on stable immunosuppressive regimens (no change in dose over the previous 30 days), who have not had a rejection episode with the last 30 days are appropriate.

From the above, it should be clear that the present invention provides improved devices and methods to measure secreted cell products, and in particular, secreted T cell cytokines. The devices and methods of the present invention provide a greater capability to detect cytokines from individual cells in a mixture of heterogeneous cells.

We claim:

1. A method of detecting T cell cytokines, comprising:
   a) providing:
      i) a cell culturing means;
      ii) a microwell comprising first and second membranes, said first membrane comprising a hydrophobic membrane having a first cytokine binding ligand;
      iii) a first sample of cells from a first human comprising T cells capable of secreting cytokines; and
      iv) a second sample of cells from a second human comprising T cells rendered substantially incapable of secreting cytokines;
   b) adding said first and second samples to said cell culturing means to create a mixture;
   c) incubating said mixture in said cell culturing means;
   d) removing said mixture from said cell culturing means;
   e) adding said mixture to said microwell under conditions such that said first sample T cells secrete a cytokine that binds to said first cytokine binding ligand; and
   f) detecting said secreted T cell cytokine.

2. The method of claim 1, wherein said detecting comprises introducing a second cytokine binding ligand into said microwell under conditions such that a colorimetric signal is generated.

3. The method of claim 1, wherein said first cytokine binding ligand comprises antibody specific for a cytokine.

4. The method of claim 3, wherein said antibody is specific for an interferon.

5. The method of claim 4, wherein said interferon is interferon gamma.

6. The method of claim 3, wherein said antibody is specific for an interleukin.

7. The method of claim 6, wherein said interleukin is IL-5.

8. The method of claim 1 wherein said first and second humans are related.

9. The method of claim 1, wherein said first and second humans are unrelated.

10. A method of detecting T cell cytokines, comprising:
    a) providing:
       i) a microwell comprising first and second membranes, said first membrane comprising a hydrophobic membrane having a first cytokine binding ligand and said second membranes supporting said first membrane; and
       ii) a sample of cells comprising T cells capable of secreting cytokines;
    b) adding said sample of cells to said microwell under conditions such that said T cells secrete a cytokine that binds to said first cytokine binding ligand; and
    c) capturing a computer readable image of said microwell.

11. The method of claim 10, wherein said first cytokine binding ligand comprises antibody specific for a cytokine.

12. The method of claim 11, wherein said antibody is specific for an interferon.

13. The method of claim 12, wherein said interferon is interferon gamma.

14. The method of claim 11, wherein said antibody is specific for an interleukin.

15. The method of claim 14, wherein said interleukin is IL-5.

* * * * *